(12) United States Patent
O'Rourke et al.

(10) Patent No.: US 11,529,472 B2
(45) Date of Patent: Dec. 20, 2022

(54) INJECTION DEVICE

(71) Applicant: NORTON HEALTHCARE LIMITED, Castleford (GB)

(72) Inventors: Douglas James O'Rourke, Cambridge (GB); Alan Sanders, Cambridge (GB); Joseph Peter Corrigan, Cambridge (GB); James Joseph Riley, Stafford (GB); Christopher John Clarke, Walton on Thames (GB)

(73) Assignee: Norton Healthcare Limited, Castleford (GB)

( * ) Notice: Subject to any disclaimer, the term of this patent is extended or adjusted under 35 U.S.C. 154(b) by 386 days.

(21) Appl. No.: 16/580,129

(22) Filed: Sep. 24, 2019

(65) Prior Publication Data
US 2020/0093993 A1    Mar. 26, 2020

(30) Foreign Application Priority Data
Sep. 24, 2018 (GB) ..................... 1815551

(51) Int. Cl.
*A61M 5/315* (2006.01)
*G16H 20/17* (2018.01)
(Continued)

(52) U.S. Cl.
CPC ........ *A61M 5/3157* (2013.01); *A61M 5/3158* (2013.01); *A61M 5/31505* (2013.01);
(Continued)

(58) Field of Classification Search
CPC ............ A61M 5/3157; A61M 5/31566; A61M 5/31565; A61M 5/31568;
(Continued)

(56) References Cited

U.S. PATENT DOCUMENTS 4,252,118 A    2/1981 Richard et al.
4,391,272 A    7/1983 Staempfli
(Continued)

FOREIGN PATENT DOCUMENTS

EP    2301599 A1    3/2011
EP    3381494 A1 * 10/2018 .......... A61M 5/3155
(Continued)

*Primary Examiner* — Bhisma Mehta
*Assistant Examiner* — Neeraja Gollamudi
(74) *Attorney, Agent, or Firm* — Blank Rome LLP

(57) ABSTRACT

Injection monitoring circuitry is provided for coupling to part of an injection device having a syringe and a plunger rod. The injection monitoring circuitry has an input to receive force measurement data from a force sensor, the force measurement data includes a plurality of timestamped force measurements of force applied by a user to the injection device when an injection is administered to an injection site. Processing circuitry is provided to determine from the force measurement data when an end of injection has been reached, the end of injection corresponding to the plunger rod having reached an end position in a distal portion of the barrel of the syringe during administration of the injection by the user. Machine readable instructions and an injection monitoring method are also provided.

13 Claims, 17 Drawing Sheets

(51) Int. Cl.
*A61M 5/50* (2006.01)
*A61M 5/31* (2006.01)
*G01L 5/00* (2006.01)
*A61M 5/32* (2006.01)

(52) U.S. Cl.
CPC ......... *A61M 5/3202* (2013.01); *A61M 5/3205* (2013.01); *A61M 5/5013* (2013.01); *A61M 2005/3126* (2013.01); *A61M 2205/332* (2013.01); *A61M 2205/3317* (2013.01); *A61M 2205/3576* (2013.01); *A61M 2205/581* (2013.01); *A61M 2205/582* (2013.01); *A61M 2205/587* (2013.01); *A61M 2205/8206* (2013.01); *G01L 5/0028* (2013.01); *G16H 20/17* (2018.01)

(58) Field of Classification Search
CPC ........ A61M 2205/332; A61M 5/31505; A61M 5/3158; A61M 5/5013; A61M 2005/3126; A61M 2205/3317; A61M 2205/3576; A61M 2205/8206; G16H 20/17
See application file for complete search history.

(56) References Cited

U.S. PATENT DOCUMENTS

| | | |
|---|---|---|
| 4,391,279 A | 7/1983 | Staempfli |
| 4,923,443 A | 5/1990 | Greenwood et al. |
| 4,950,243 A | 8/1990 | Estruch |
| 5,032,114 A | 7/1991 | Olovson |
| 5,059,179 A | 10/1991 | Quatrochi et al. |
| 5,078,686 A | 1/1992 | Bates |
| 5,084,017 A | 1/1992 | Maffetone |
| 5,125,899 A | 6/1992 | Frignoli |
| 5,562,623 A | 10/1996 | Shonfeld et al. |
| 6,129,712 A | 10/2000 | Sudo et al. |
| 2016/0259913 A1 | 9/2016 | Yu et al. |
| 2017/0165423 A1 | 6/2017 | Holland |
| 2017/0312430 A1* | 11/2017 | Schleicher .......... A61M 5/1723 |
| 2018/0211562 A1 | 7/2018 | Rios et al. |
| 2018/0333543 A1 | 11/2018 | Diaz et al. |
| 2018/0369481 A1 | 12/2018 | Pedersen et al. |
| 2019/0009029 A1 | 1/2019 | Fabricius et al. |
| 2019/0255252 A1* | 8/2019 | Gentz .................. A61M 5/315 |

FOREIGN PATENT DOCUMENTS

| | | | |
|---|---|---|---|
| EP | 3381494 A1 | 10/2018 | |
| KR | 200450065 Y1 | 9/2010 | |
| KR | 200451044 Y1 | 11/2010 | |
| WO | 2006045215 A1 | 5/2006 | |
| WO | 2014029683 A1 | 2/2014 | |
| WO | WO-2017070391 A2 * | 4/2017 | .......... G09B 23/285 |
| WO | 2018125887 A2 | 7/2018 | |
| WO | 2018138051 A1 | 8/2018 | |

* cited by examiner

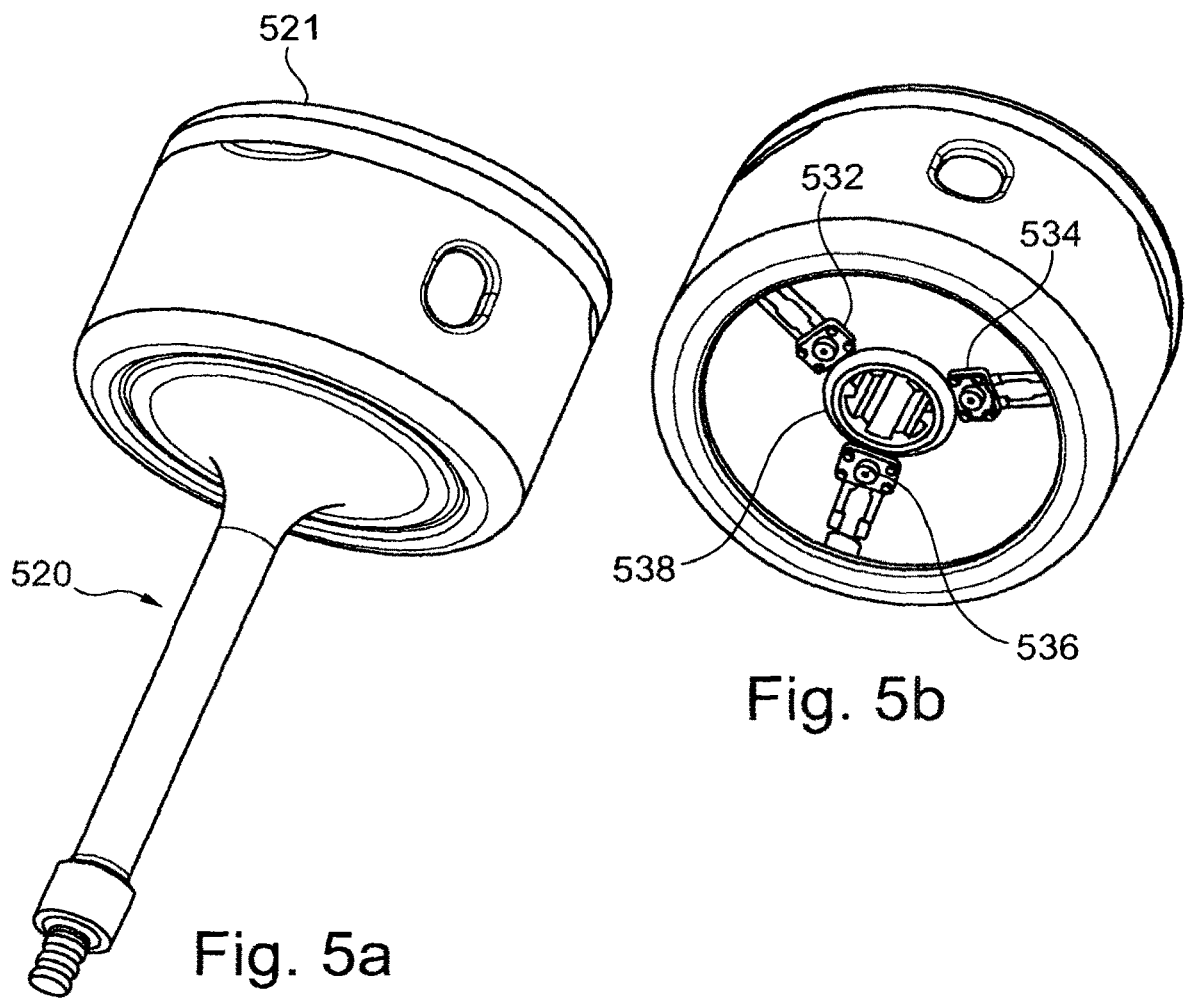
Fig. 5a
Fig. 5b
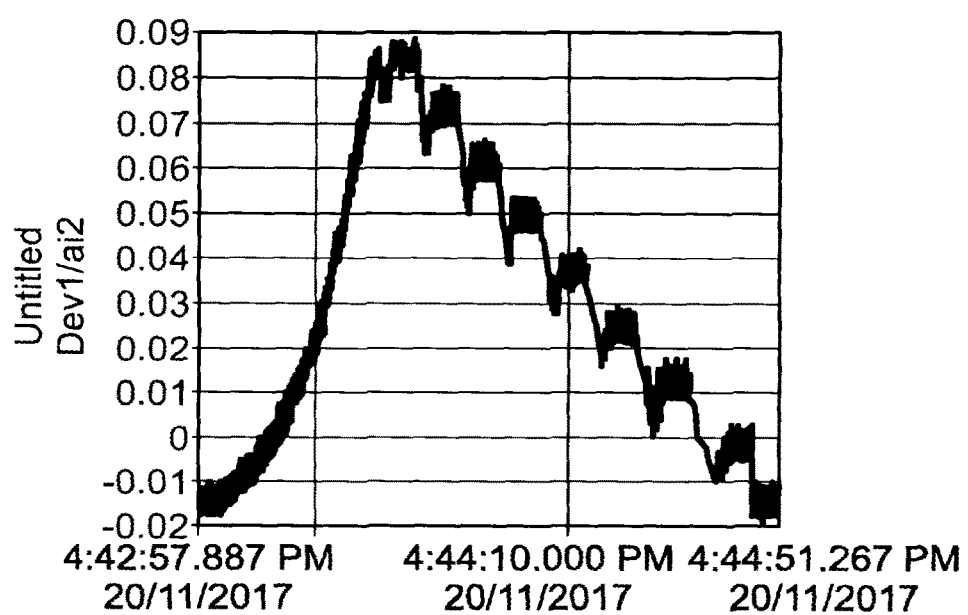
Fig. 5c

INJECTION DEVICE

BACKGROUND OF THE INVENTION

Field of the Invention

This disclosure relates to the field of injection devices for delivering medicament, in particular to injection monitoring circuitry for injection devices, which may be installed for example, in a plunger rods for an injection device such as prefilled syringes.

Description of the Related Art

Effective medical treatment often relies upon patient adherence to a particular dosage regime prescribed by a healthcare provider, the regime involving taking a complete dose at a specified frequency for a specified duration of time. However, ensuring patient adherence to prescribed medication regimes is often a challenge for medicaments that are self-administered. Injection devices such as prefilled syringes are widely used to supply patients with medicaments for self-administration. Prefilled syringes are also often used in clinical trials because of their simplicity relative to autoinjectors.

Reliable automated gathering of data each time a medicament dose is taken by a user of an injection device is of interest to healthcare providers, injection device manufacturers and pharmaceutical companies. This has the advantage of reducing reliance on patient recollection and truthfulness when correlating treatment efficacy with a given medication regime. There is an incentive to ensure that data is gathered every time a medicament dose is administered and to determine whether or not a complete dose has been administered. It may also be useful to provide user with feedback regarding successful and unsuccessful injections and with regard to their own injection technique.

SUMMARY OF THE INVENTION

In accordance with a first aspect of the present invention there is provided injection monitoring circuitry for coupling to part of an injection device having a syringe and a plunger rod, the injection monitoring circuitry including an input to receive force measurement data from a force sensor, the force measurement data including a plurality of timestamped force measurements of force applied by a user to the injection device when an injection is administered to an injection site. The injection monitoring circuitry further includes a processing circuitry configured to determine from the force measurement data when an end of injection has been reached, the end of injection corresponding to the plunger rod having reached an end position in a distal portion of the barrel of the syringe during administration of the injection by the user.

The processing circuitry is configured to determine when the end of injection has been reached without using reflection-based measurements of displacements of the plunger rod relative to a body of the syringe.

According to the present technique, timestamped force measurements are analysed by processing circuitry to reliably determine whether or not an injection event has been successful in delivering a complete dose of a medicament. Analysis of the timestamped force measurement data may be used to provide feedback to a user of an injection device, promoting improved injection technique as might be expected from an expert user rather than an average user. Analysis of the timestamped force data may be used to discriminate between an end of injection where a complete dose has not been delivered (unsuccessful injection) and an end of injection where a complete dose has been delivered (successful injection).

It has been recognized that analysis of the timestamped force measurements can be used to make a reliable determination of whether or not a complete dose of a medicament has been delivered. This makes provision of a displacement sensor such as a reflection-based displacement sensor to determine by direct measurement a relative displacement of a plunger rod relative to a distal end of a syringe barrel optional unnecessary and thus simplifies manufacture and reduces cost and improves the robustness of the associated injection device to damage in use. The analysis of time-stamped force measurement data according to the present technique is readily adaptable to the inherent variability of the way in which average users of an injection device administer an injection. It is less prone to error than an electromechanical means of determining an end of injection.

In some embodiments of the injection monitoring circuitry, the processing circuitry is configured to determine the end of injection from a force profile for an injection administering event, the force profile includes an ordered time series of the plurality of timestamped force measurements.

In some embodiments of the injection monitoring circuitry, the processing circuitry is configured to determine from the force profile at least one of: a start of injection corresponding to a start of a transfer of a medicament from the syringe barrel to the injection site, a duration of the injection and whether or not a full dose of a medicament has been delivered at by the end of the injection.

In some embodiments of the injection monitoring circuitry, the processing circuitry is configured to determine the end of injection when a force measurement towards an end of the ordered time series of the force profile exceeds a force threshold value.

In some embodiments of the injection monitoring circuitry, the processing circuitry is configured to determine the end of injection depending on a comparison of a gradient of a characteristic curve fitted to the force profile with a gradient threshold value or when the gradient of the characteristic curve increases by more than a threshold amount within a predetermined time period.

In some embodiments of the injection monitoring circuitry, the processing circuitry is configured to determine a displacement of the plunger rod within the syringe as a function of time by integrating an area under a characteristic curve fitted to the force profile.

In some embodiments of the injection monitoring circuitry, the end of injection is determined using at least one of: wavelet convolution of the force profile and Fourier analysis of the force profile.

In some embodiments of the injection monitoring circuitry, the processing circuitry is configured to implement a state machine on the force profile to determine at last one of a possible injection start time and a possible injection end time.

In some embodiments of the injection monitoring circuitry, the state machine is configured to at least one of: determine the possible start depending on detection of a first predetermined number of time steps above a first threshold force within a first time window; and to determine the possible end depending on detection of a second number of time-steps below a second threshold force within a second time window.

In some embodiments of the injection monitoring circuitry, the state machine is configured to determine a mid-injection phase of the force profile depending on a third number of time-steps being above a third threshold force within a time window which includes a third number of contiguous time-steps.

In some embodiments of the injection monitoring circuitry, the processing circuitry is configured to determine the end of injection by implementing one of a machine learning algorithm and a neural network algorithm.

In some embodiments of the injection monitoring circuitry, the processing circuitry is configured to determine the end of injection by implementing a machine learning algorithm on an analysis time window of the force profile selected based on the possible injection start time and the possible injection end time determined by the state machine.

In some embodiments of the injection monitoring circuitry, the processing circuitry is configured to implement the machine learning algorithm to analyse a plurality of predetermined features of the force profile in the analysis time window to determine the end of injection, the predetermined features including at least a subset of: an injection duration; a mean force magnitude; a standard deviation of force measurements; a skew of force measurements; a kurtosis of force measurements; a maximum force value; a minimum force value; a $25^{th}$ percentile value; and a $75^{th}$ percentile value.

In some embodiments of the injection monitoring circuitry, the processing circuitry is configured to implement the machine learning algorithm to analyse a plurality of predetermined features of the force profile in the analysis time window by sub-dividing the analysis time window into a plurality of time intervals and performing the features analysis for at least one of the predetermined features independently for each of at least two of the plurality of time intervals.

In some such embodiments of the injection monitoring circuitry, the at least one predetermined feature independently analysed for the at least two time intervals is a mean force in the time interval or a standard deviation of the force in the time interval.

In some embodiments of the injection monitoring circuitry, the processing circuitry is configured to scale the force measurement data using at least one scaling factor, the scaling factor being selected depending on a form factor of a wirelessly connected display device remote from the injection device on which a force profile incorporating the force measurement data is to be displayed.

In some embodiments of the injection monitoring circuitry, the processing circuitry is configured to determine an injection hold time corresponding to a duration that a needle of the syringe is to remain in an injection site after the end of the injection and to output an indication of the injection hold time to the user.

In accordance with a second aspect of the present invention there is provided a plunger rod for an injection device, the plunger rod includes the injection monitoring circuitry of any embodiment of the first aspect of the invention.

In some embodiments of the plunger rod, at least a portion of the injection monitoring circuitry is provided in a proximal head of the plunger rod.

In accordance with a third aspect of the present invention there is provided machine readable instructions provided on a transitory or non-transitory machine-readable medium, the machine-readable instructions upon execution by one or more processing hardware circuits to receive force measurement data from a force sensor, the force measurement data including a plurality of timestamped force measurements of force applied by a user to the injection device when an injection is administered to an injection site; and determine from the force measurement data when an end of injection has been reached, the end of injection corresponding to the plunger rod having reached an end position in a distal portion of the barrel of the syringe during administration of the injection by the user; and output an end of injection indication to a user.

Machine readable instructions include instructions to determine the end of injection from a force profile for an injection administering event, the force profile including an ordered time series of the plurality of timestamped force measurements.

Machine readable instructions include instructions to implement a state machine on the force profile to determine a possible injection start time and a possible injection end time.

In some embodiments of the machine readable instructions, the state machine is to at least one of: determine the possible start depending on detection of a first predetermined number of time steps above a first threshold force within a first time window; and to determine the possible end depending on detection of a second number of time-steps below a second threshold force within a second time window.

Machine readable instructions, wherein the state machine is to determine a mid-injection phase of the force profile depending on a third number of time-steps being above a third threshold force within a time window including a fourth number of contiguous time-steps greater than the third number.

Some embodiments of the machine readable instructions include instructions to determine the end of injection by implementing one of a machine learning algorithm and a neural network algorithm.

Some embodiments of the machine readable instructions include instructions to determine the end of injection by implementing a machine learning algorithm on an analysis time window of the force profile selected based on the possible injection start time and the possible injection end time determined by the state machine.

Employing the machine learning algorithm according to some embodiments provides adaptability to inherent variation in the injection technique of the average user and offers tuning of a desired level of accuracy in the prediction of whether or not an injection event has been successful in delivering a complete intended dose of a medicament. The machine learning algorithm analyses the timestamped force measurement data with an accuracy at least as good as an expert human user analysing a force profile by eye and thus has the potential to elevate the average user to an expert user via, for example, feedback from the injection monitoring circuitry. Once available, the information on the predicted successful outcome or otherwise of individual injection events may be conveniently provided via a networked communication system to a health professional to monitor compliance of a patient with a prescribed treatment regime.

Some embodiments of the machine readable instructions include instructions of the machine learning algorithm to analyse a plurality of predetermined features of the force profile in the analysis time window to determine the end of injection, the predetermined features including at least a subset of: an injection duration; a mean force magnitude; a standard deviation of force measurements; a skew of force measurements; a kurtosis of force measurements; a maximum force value; a minimum force value; a 25$^{th}$ percentile value; and a 75$^{th}$ percentile value.

Some embodiments of the machine readable instructions include instructions of the machine learning algorithm configured to sub-divide the analysis time window into a plurality of sub-windows and to perform the features analysis for at least one of the predetermined features independently for each of at least two of the plurality of sub-windows.

Dividing up the analysis window into discrete time intervals and independently determining statistical parameters for sub-windows simplifies implementation of the machine learning model, making the algorithm more efficient and making it easier to deploy more sophisticated analysis in processing circuitry in the plunger rod. This may improve the level of and accuracy of feedback available to the user in real-time on appropriate injection technique.

In some embodiments of the machine readable instructions, the at least one predetermined feature independently analysed for the at least two sub windows is a mean force in the sub-window or a standard deviation of force in the sub-window.

In accordance with a third aspect of the present invention there is provided a method of monitoring an injection event performed by an injection device including a plunger rod and a syringe, the method including receiving force measurement data from a force sensor, the force measurement data includes a plurality of timestamped force measurements of force applied by a user to the injection device when an injection is administered to an injection site; determining from the force measurement data when an end of injection has been reached, the end of injection corresponding to the plunger rod having reached an end position in a distal portion of a barrel of the syringe during administration of the injection by the user; and outputting an end of injection indication to a user.

Further aspects, features and advantages of the present invention will be apparent from the following description of preferred embodiments with reference to the accompanying drawings.

BRIEF DESCRIPTION OF THE DRAWINGS

FIGS. 5a and 5b schematically illustrate an example plunger rod having a set of micrometer-scale devices (MEMS) as force sensors;

FIG. 5c schematically illustrates a voltage against time responsiveness for the MEMS force sensors of FIG. 5b when deployed in a test rig;

DETAILED DESCRIPTION OF THE INVENTION

Figure 1:
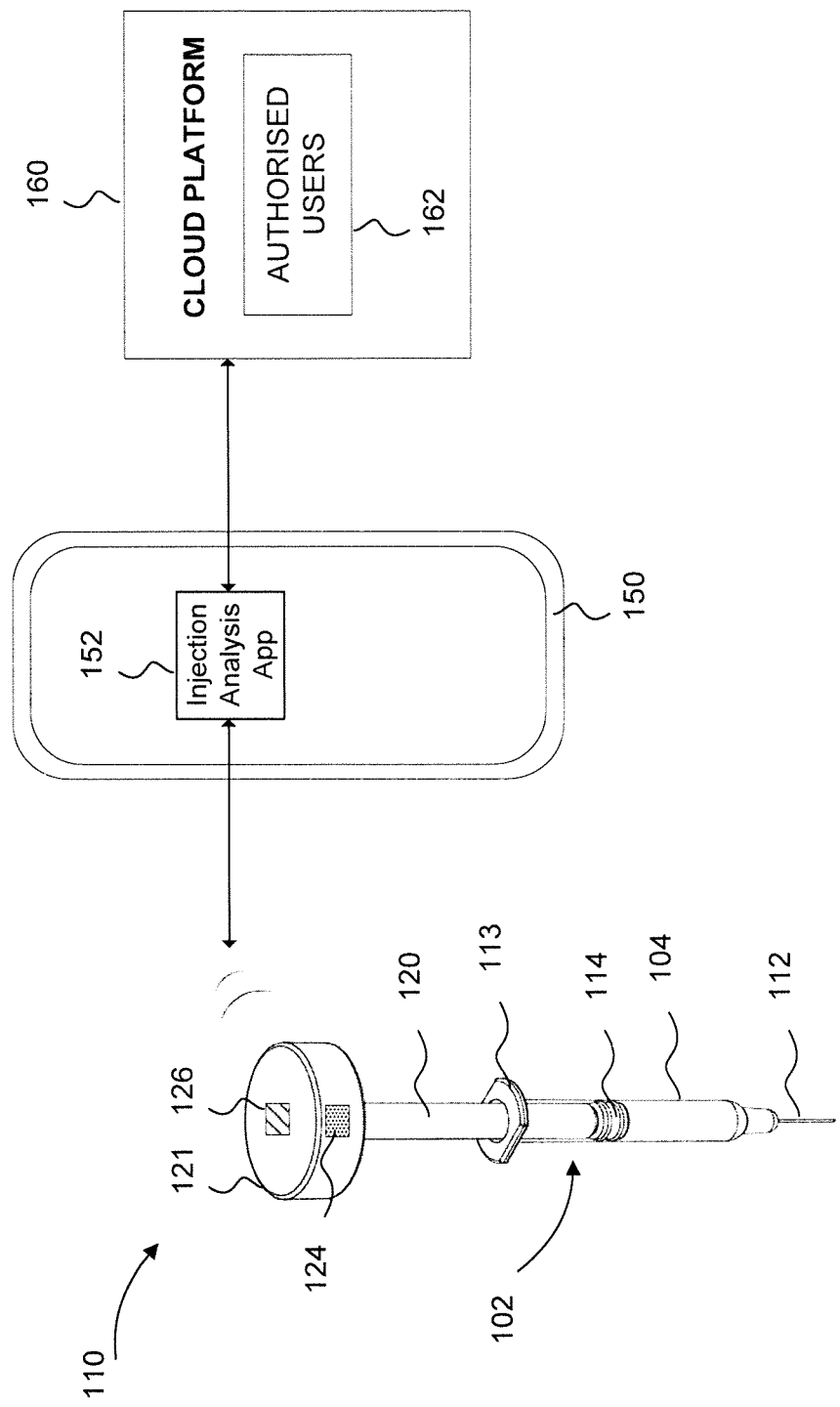
FIG. 1 schematically illustrates an injection system according to the present technique.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. The term includes syringes of all types, devices that contain said syringes such as auto-injectors, pen-injectors, patch injectors and other similar devices.

The term "user" may refer to a medical practitioner, end user or other user associated therewith.

The terms "coupled" or "coupling" may refer to any connection between components (not necessarily a direct connection; there may be intermediate components therebetween i.e. an indirect connection) that enables a force to be transmitted between the components. The connection may be temporary and the components need not be physically or mechanically attached to one another.

The term "plunger rod" may refer to a plunger rod, piston rod or plunger stem which can be coupled to a stopper or piston that is axially moveable in a barrel to expel medicament from the injection device. The plunger rod may incorporate a proximal head;

The terms "forward" or "forwards" or "distal" may refer to a direction towards the end of the injection device from which medicament is expelled.

The terms "backward", "backwards", "rearwards" or "rearwardly" or "proximal" may refer to a direction away from the end of the injection device from which medicament is expelled.

The term "plunger-down orientation" may mean an orientation in which the injection device is held with its distal end, i.e. the needle end, pointing upwards and its proximal end, i.e. the plunger end, pointing downwards.

The term "medicament" may include a substance in liquid or gas form. The medicament may be selected from the group of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying antirheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

When referring to the injection device, the term "containing the medicament", may refer to the medicament being contained within a suitable medicament container, such as a pre-filled syringe or cartridge, within the injection device.

The term "friction fit" may include any type of interference fit or press fit wherein a fastening between components is achieved by friction when the components are pressed together.

The term "snap fit" may include any type of fastening between components achieved by pushing together interlocking parts of the components, including push to connect compression fittings.

The term "circuitry" refer to general purpose processing circuitry configured by program code to perform specified processing functions. The circuitry may also be configured by modification to the processing hardware. Configuration of the circuitry to perform a specified function may be entirely in hardware, entirely in software or using a combination of hardware modification and software execution. Program instructions may be used to configure logic gates of general purpose or special-purpose processing circuitry to perform a processing function.

Circuitry may be implemented, for example, as a hardware circuit including custom Very Large Scale Integrated, VLSI, circuits or gate arrays, off-the-shelf semiconductors such as logic chips, transistors, or other discrete components. Circuitry may also be implemented in programmable hardware devices such as Field Programmable Gate Arrays, FPGA, programmable array logic, programmable logic devices, A System on Chip, SoC, or the like.

Machine-readable program instructions may be provided on a transitory medium such as a transmission medium or on a non-transitory medium such as a storage medium. Such machine-readable instructions (computer program code) may be implemented in a high level procedural or object-oriented programming language. However, the program(s) may be implemented in assembly or machine language, if desired. In any case, the language may be a compiled or interpreted language, and combined with hardware implementations. Program instructions may be executed on a single processor or on two or more processors in a distributed manner.

The term "timestamped data" may refer to data having in which each data entry is an absolute timestamp in, for example, in hours:minutes:seconds format. Alternatively, one or more timestamp data entry of the timestamped data may refer to data from which an absolute time can be derived relative to a reference time. The reference time (absolute timestamp) may be included in the timestamped data together with a plurality of corresponding relative timestamps. One or more of the timestamps may also include a calendar date. Thus the timestamped data may include one or more temporal sequences of timestamped measurements where a given sequence may include one or more absolute timestamps, one or more relative timestamps or a combination of absolute and relative timestamps. A given sequence may include a timestamp indicating a calendar date on which measurements were captured. The calendar day may be specified as a separate data point within the timestamped data or alternatively may be included in an absolute timestamp data entry.

Smart injection systems capable of wirelessly transmitting data from an injection device to a remote analysis device are known. However, the known smart injection systems are high cost, reusable devices and tend to have niche use and to be produced in low volumes in comparison to, for example, prefilled syringes. Measurement of displacement of an injection device plunger rod relative to a syringe barrel to determine whether or not a complete dose of a medicament has been delivered during administering of an injection may involve incorporation of a displacement sensor such as an optical sensor or an ultrasound sensor in a cap of the plunger rod and the displacement sensor may calculate displacement by reflection of light or ultrasound from, for example, a proximal flange of the syringe. However, measuring displacement using specific sensors such as optical or ultrasound sensors adds to the complexity and to the cost of the injection device.

Electromechanical techniques to determine that an end of injection has been reached with a complete dose having been delivered may rely upon specific adaptation of a syringe body to detect that a plunger rod has reached the end of the barrel. Alternative techniques may rely on precisely arranging mechanical features of the injection device to trigger an electrical connection when a force corresponding to an end of injection has been reached. However, given the inherent variability in the way that different users apply force and even given variability for the same user for different injection events, electromechanical means of determining an end of injection are prone to error.

According to the present technique, a time series of force measurement data from a force sensor can be analysed to more reliably determine that a complete dose of a medicament has been delivered for a given injection event and the level of accuracy can be readily quantified. Furthermore, an injection complete notification can be conveniently notified to a user via at least one of visible, audible and haptic feedback.

Thus, according to the present technique, displacement is to be determined indirectly using force sensor measurements to simplify manufacture of and reduce cost of the smart injection device. It is possible to determine that a complete dosage of a medicament has been delivered and that the plunger rod of an injection device has reached an end position in a distal portion of a barrel of a syringe using measurements from a force sensor without providing an additional displacement sensor, such as a displacement sensor that performs light or ultrasound reflection measurements.

FIG. 1 schematically illustrates an injection system according to the present technique. The system includes an injection device 110, a user device 150 capable of wireless communication with the injection device 110 and a cloud platform 160 including one or more computing devices with which the user device 150 may communicate via a computer network. The user device 150 includes an injection analysis program application, an "App", installed thereon to handle data exchanged wirelessly with the injection device 110. The cloud platform 160 may collate and store information uploaded from the injection device 110 and may provide a repository of injection data for use by at least one of the injection analysis app 152 and the injection device 110 or for analysis independently of the injection device 110. Injection analysis information stored on the cloud platform 160 may include at least one of: an injection device identifier, a battery status of the injection device 110, a force profile, which is a relationship between applied force and time, associated with an injection event performed using the injection device 110. Thus, the force profile may include one or more timestamps, which may include absolute time stamps, relative timestamps or a combination thereof. The injection information stored on the cloud-based platform 160 may be access-controlled such that it is accessible only to a restricted set of authorised users 162. The set of authorised users may be configurable by the system.

The injection device 110 includes a syringe 102 having a syringe barrel 104, a needle 112, a flange 113 and a resilient stopper 114. The injection device further includes a plunger rod 120 having a proximal head 121. Previously-known injection devices include pre-filled injection devices in which the syringe barrel 104, which forms a barrel to enclose a volume of medicament for injection, may be supplied containing a reservoir of a medicament. Such pre-filled injection devices may be supplied with a plunger rod already functionally engaged with a stopper and thus ready for use to inject the medicament by pressing the plunger rod to urge it from the proximal to the distal end of the syringe barrel 104 to expel the medicament through the needle 112 into an injection site. In some syringes the stopper is an integral part of the plunger rod, but in other syringes the plunger rod and stopper may be separate components and the stopper may be releasably attached to the plunger rod. For example, the stopper may have a screw-threaded hole on its proximal side, into which the distal end of the plunger rod may be screwed to attach the stopper and plunger rod such that they can be moved in unison.

The syringe 102 may be provided with an aperture to receive a needle 112 at the distal end of the syringe barrel 104 or may alternatively be provided with the needle 112 already in place.

To deliver a dose of a medicament using the injection device 110, the user may apply a force by pressing the proximal head 121 of the plunger rod 120, pushing the plunger rod 120 axially into the syringe barrel 104. This pushes the resilient stopper 114 from the proximal end to the distal end of the syringe barrel 104, causing medicament to be delivered to an injection site through the needle 112. The syringe barrel 104 forms a vessel for containing a dose of a medicament.

Figures 2A, 2B:
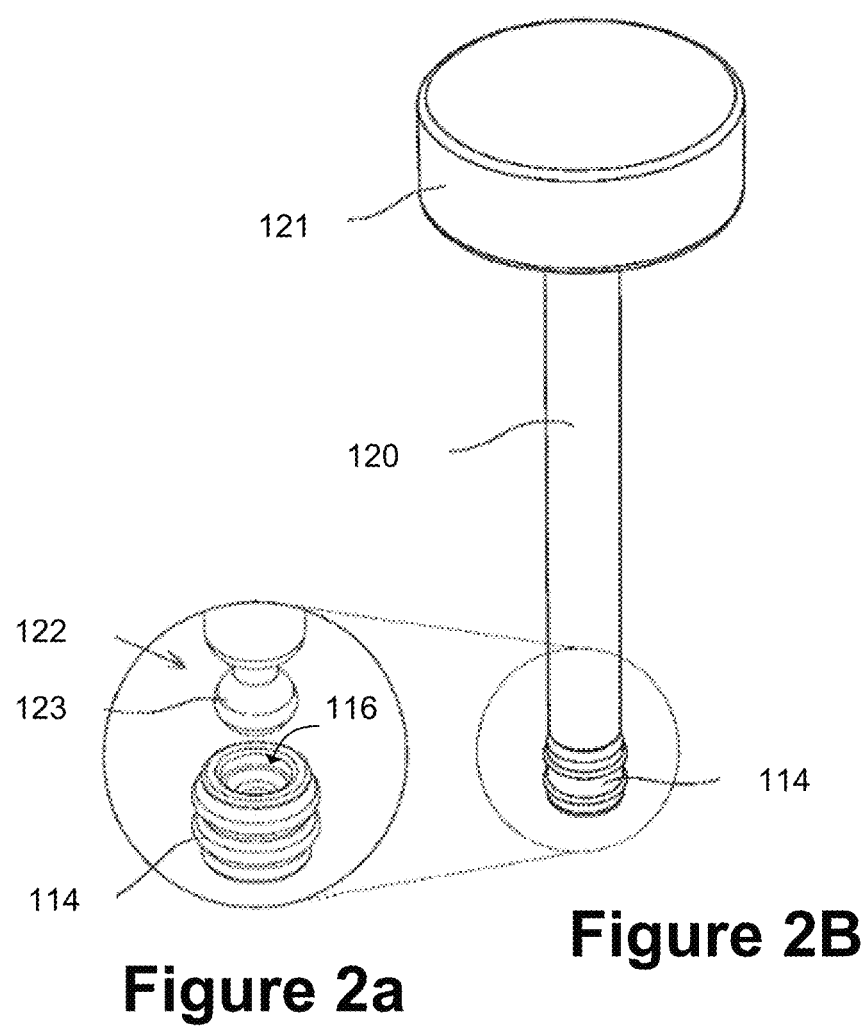
FIGS. 2A and 2B schematically illustrate a distal plunger rod end and a co-operating resilient stopper of an injection device.

According to the present technique, the plunger rod 120 is a separate component from the resilient stopper 114 and may be releasably connected to the stopper 114 prior to administration of an injection. Thus, the syringe 102 may be supplied as a pre-filled syringe including the stopper 114 to retain the medicament in the syringe barrel 104. Provision of the resilient stopper albeit without a plunger rod provides at least a partial seal against exposure of the medicament to air from the surrounding environment and thus maintains the integrity of the medicament during storage and prior to injection. The plunger rod 120 of the example of FIG. 1 may be attached to the stopper 114 in any one of a number of different ways. The attachment mechanism between a proximal end of the plunger rod 120 and the stopper 114 may be a mechanical attachment mechanism such as, for example, a screw thread and complementary screw-threaded hole. In one alternative to the screw-threaded engagement between the proximal end of the plunger rod 120 and the stopper, the engagement may be a friction-fit or snap fit as illustrated in FIGS. 2A and 2B. In a further alternative, the attachment between the proximal end of the plunger rod 120 and the stopper 114 may include or include a magnetic attachment mechanism as illustrated in the FIG. 2C example. The plunger rod 120 may be detached from the stopper 114 following administration of an injection and may be re-used with one or more other pre-filled syringes. The plunger rod 120 is compatible with pre-filled syringes but may also be used with syringes that are not pre-filled provided that a suitable stopper is used to engage the plunger rod 120 in the syringe barrel of the syringe to be used. In implementations in which the syringe is not pre-filled, the plunger rod 120 and resilient stopper 114 may be integrally formed or supplied together as an assembled multi-part unit.

The proximal head 121 of the plunger rod 120 in this example includes a force sensor 124 and a set of injection monitoring circuitry 126. The injection monitoring circuitry 126 is arranged to receive force measurement data from the force sensor 124, the force measurement data including a plurality of timestamped force measurements representing a force applied by a user to the injection device 110 during an injection event when an injection is administered to an injection site. The injection monitoring circuitry 126 executes program instructions to determine from the force measurement data when an end of injection has been reached and whether or not a complete dose of a medicament has been delivered. The end of injection may correspond to the plunger rod 120 having reached an end position in a distal portion of a barrel of the syringe 102 during administration of an injection by a user. In the example arrangement of FIG. 1 the force sensor 124 and the injection monitoring circuitry 126 are disposed in the proximal head 121 of the plunger rod 120, but each of these components may be disposed at a different location on the plunger rod 120 and yet perform the same function. In some examples, a top surface of the proximal head 121 may be provided with a screen to display visual indications to a user regarding an injection status and/or a device status.

FIG. 2A shows a distal plunger rod end 122 of the plunger rod 120 and the resilient stopper 114 in a disassembled state. FIG. 2B shows the plunger rod 120 and the resilient stopper in an assembled state. The distal plunger rod end 122 may be provided with a spherical portion 123, as illustrated in FIG. 2A. The resilient stopper 114 in this example is a standard prefilled syringe stopper having a screw-threaded recess 116. The spherical portion 123 may alternatively be an oblate sphere or a more irregular rounded three-dimensional shape to cooperate with the resilient stopper 114 by engaging with it to allow the resilient stopper 114 to be moved axially towards the distal end of the syringe barrel 104. The resilient stopper 114 may be provided in the syringe barrel 104 of a prefilled syringe and the plunger rod 120 may be engaged with the resilient stopper prior administration of an injection by the user.

The spherical portion 123 of the distal rod end 122 may have a maximum diameter designed to enable it to be engaged with the screw-threaded recess 116 by a simple friction-fit or snap-fit. The resilience of the stopper 114 material facilitates this. Instead of the screw-threads of the recess 116 serving their usual function (receiving a screw-threaded distal rod end), the screw-threads may in some examples serve as relatively small, elastic or resilient ribs which may engage the incoming spherical portion 123, helping to lightly retain it within the recess 16.

To attach the plunger rod 120 to the resilient stopper 114, the user may insert the distal rod end 122 into the proximal end of the syringe barrel 104 and push axially forwards towards the needle 112 until the spherical portion 123 is engaged in the stopper recess 116. This is quicker and simpler than the prior art technique of rotating a screw-threaded rod into the screw-threaded recess 116.

To deliver a dose of medicament, the user presses on the proximal head 121 whereupon a forward axial force is transmitted through the spherical portion 123 of the distal rod end 122 to the stopper 114 which, in turn, moves axially forwards to expel medicament from the needle 112.

The coupling between the distal rod end 122 and the stopper 114 need only be sufficient to enable transmission of the forward axial force. The components need not be physically connected together. In some examples, the screw-threads of the recess 116 may only lightly retain the spherical portion 123 of the distal rod end, but with a force that can be easily overcome by a rearward axial movement of the plunger rod 120. Thus the rearward axial motion of the plunger rod 120 may result in the stopper 114 remaining in the syringe barrel 104 once the plunger rod 120 has been fully extracted from the syringe barrel 104 with an exposed spherical portion 123 devoid of the stopper 114 In other examples, the rearward axial movement of the plunger rod 120 in the syringe barrel 104 withdraws the resilient stopper 114 completely out of the syringe barrel 104 together with the plunger rod 120, where the resilient stopper it can be manually detached from the spherical portion and discarded prior to reuse of the plunger rod 120 with a different syringe, such as a prefilled syringe incorporating a further resilient stopper compatible with the plunger rod 120.

Figure 2C:
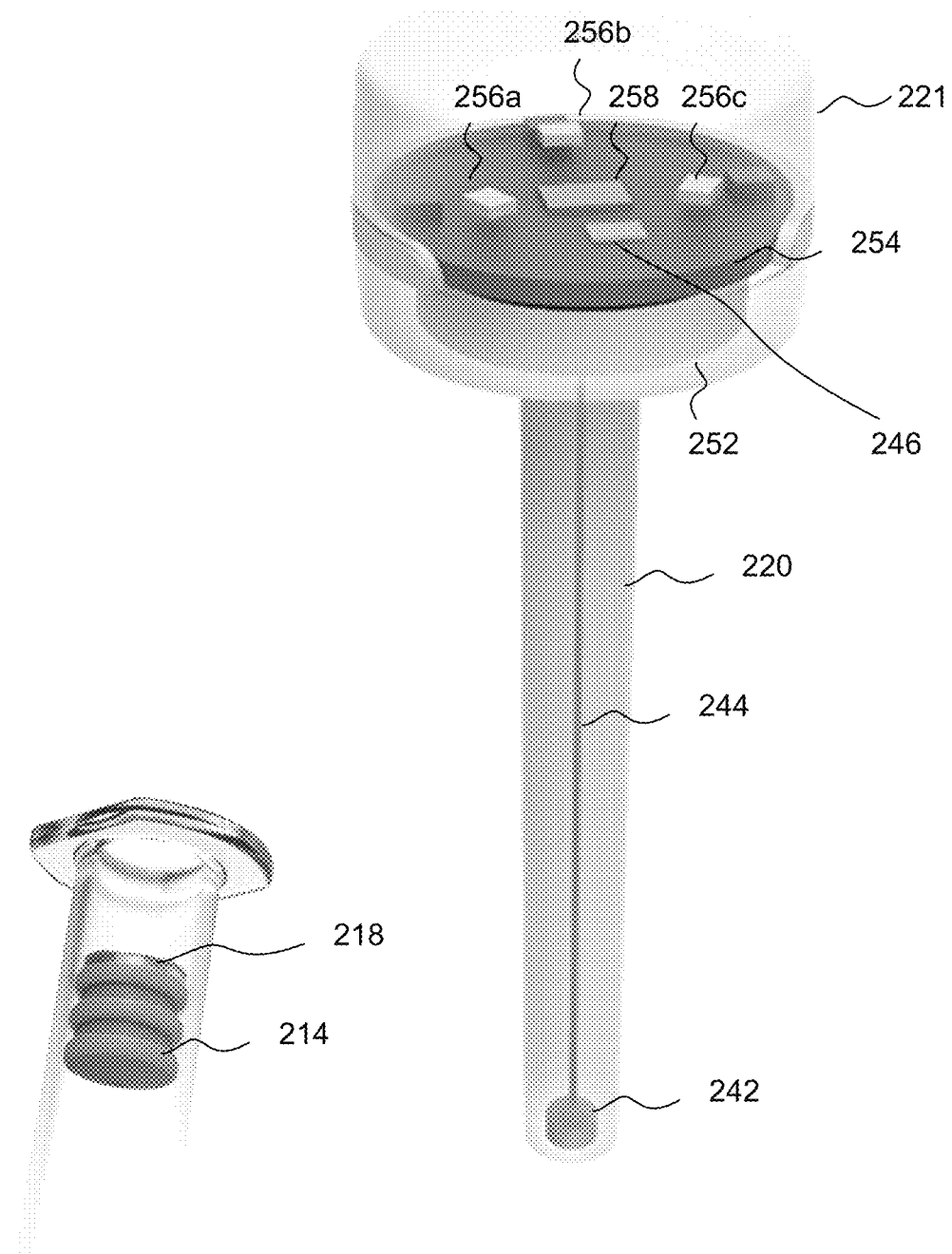
FIG. 2C schematically illustrates an example plunger rod having a magnetic coupling with a resilient stopper of an injection device.

FIG. 2C schematically illustrates an alternative example of a plunger rod 220 relative to example of FIGS. 2A and 2B. The plunger rod 220 of FIG. 2C has a magnetic attachment mechanism rather than a primarily mechanical attachment mechanism. The plunger rod 220 includes: a proximal head 221; a stopper-engaging element 242 of magnetic material; a conductive rod 244; a Hall-effect sensor 246; a battery 252; a Printed Circuit Board (PCB) 254; a set of Microelectromechanical (MEMS) force sensors 256a, 256b, 256c; and a processor 258.

The stopper-engaging element 242 in this example is located at a distal end of the plunger 220 and is arranged to magnetically couple to a resilient stopper 214 provided in a syringe barrel. The resilient stopper 214 may be a conventional stopper 214 adapted to include a magnet insert 218. Alternatively, a resilient stopper may be provided having an integrally formed magnet or the stopper 214 may be formed from a resilient material containing suspended magnetic particles (e.g. a rubber magnet) such that it generates a magnetic field to enable coupling to the stopper-engaging element 242 provided in the distal end of the plunger rod.

The magnet 218 may be a permanent magnet at room temperature. However, an electromagnet could alternatively be used. Examples of magnetic materials that may be used to form the stopper-engaging element include iron, nickel, cobalt and steel. The strength of the stopper-engaging element 242 of the plunger rod 220 and the magnetic field strength generated by the resilient stopper 214 and/or magnet insert 218 may be adapted according to a desired coupling force. At a minimum, the coupling force may be sufficiently strong to allow the plunger rod 220 to engage with the resilient stopper 214 to efficiently and effectively deliver a full dose of a medicament to an injection site. The magnetic insert 218 may conveniently provide a snap-coupling or a friction fit or a screw fit to the resilient stopper 214, which promotes easy assembly of the injection device.

The plunger rod 220 and the magnetic stopper 214 may be detached from each other when an injection dose is complete by a user pulling the plunger rod axially back though the syringe barrel 104 (see FIG. 1). In some examples, the magnetic stopper 214 may release from the stopper-engaging element 242 of the plunger rod 220 during the reverse axial motion of the plunger rod 220 in the syringe barrel 104. In alternative examples, the resilient stopper may be drawn out of the syringe barrel 102 together with the plunger rod 220 and then manually detached from the plunger rod 220. The plunger rod 220, may then be re-used for a subsequent injection event, for example using a different pre-filled syringe.

The conductive rod 244 may extend axially along the plunger rod 220 from the distal end, to electrically connect the stopper-engaging element 242 to the PCB 254. This allows the Hall-effect sensor 246 to detect the initiation of magnetic coupling between the permanent magnet 218 and the stopper-engaging element 242 and to automatically switch the plunger rod 220 into an active electronic state in which it is ready to capture force data relevant to an injection event. The Hall-effect sensor 246 is arranged to switch on in response to the presence of, for example, a threshold magnetic field. When the Hall-effect sensor switches on, it switches on the circuitry of the PCB 254, powering up the processor 258 ready to process data and triggering the MEMS force sensors 256a, b, c to be in a state ready to detect force applied to the proximal head 221 of the plunger by a user.

The Hall-effect sensor 246 generates an output electrical signal in response to the presence of a magnetic field, which in this example, is the magnetic field generated by the magnetic insert 218. Thus, the Hall-effect sensor 246 switches on in response to the magnetic insert 218 (and thus the resilient stopper 214) being brought sufficiently close to the stopper-engaging element 242 of the plunger rod 220 for the components to magnetically couple. The Hall-effect sensor 246 is just one example of a switch to switch on the injection monitoring circuitry including the force sensors 256a, b, c and alternative switches may be used. Example alternatives to the Hall-effect sensor 246 are magnetometers, and reed switches. Further alternatives include inductive switches, capacitive switches, light sensing switches, radar, and contacting mechanical switches.

The Hall-effect sensor 246 has a benefit that it can detect a static magnetic field whereas an inductive switch would be responsive to relative movement and not to a static field.

Operation of the Hall-effect sensor 246 as a switch to switch on the injection monitoring circuitry specifically upon coupling between the plunger rod 220 and the syringe stopper 214, 218 may rely on the magnet 218 being in the stopper 214. However, for alternative switching arrangements that implement magnetic coupling, a permanent magnet could be provided in the plunger rod 220 and a magnetic material could be provided in, or as an insert to, the resilient stopper 214.

In the example arrangement of FIG. 2C, the stopper-engaging element 242 moves as the plunger rod moves from the proximal towards the distal end of the syringe barrel. When the stopper-engaging element 242 of the plunger rod 220 gets sufficiently close to the magnet 218 in the resilient stopper 214 to form a magnetic connection, the Hall-effect sensor generates a voltage and switches on the processor 258 and force sensors 256a, b, c. The battery 252 may provide power to components of the PCB 254 such as the processor 258 and the force sensors 256a, 256b, 256c. The battery 252 may be a replaceable battery or a rechargeable battery. The processor 258 may have control circuitry to switch it between a plurality of different power levels. The plurality of power levels may include at least one sleep state and at least one active state. The injection monitoring circuitry of the processor 258 may be placed in a sleep state when the Hall-effect sensor is switched off.

Figure 3:
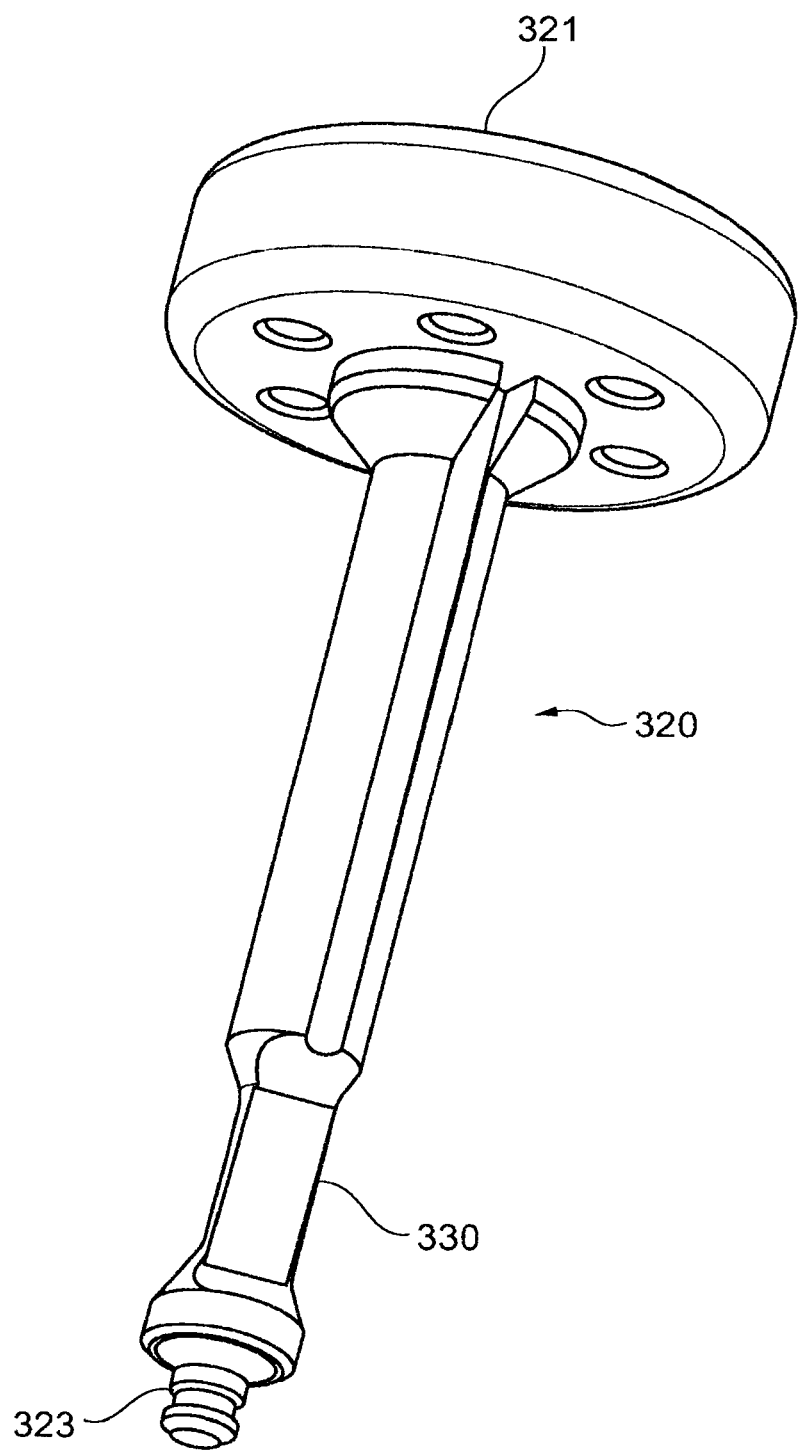
FIG. 3 schematically illustrates a plunger rod for an injection device having a strain gauge provided at its distal end, close to a stopper-engaging portion.

FIG. 3 schematically illustrates a plunger rod for an injection device having a strain gauge 330 provided at its distal end, close to a stopper engaging portion 323. The strain gauge 330 is one example of a force sensor. The strain gauge 330 may be attached to an external surface of the plunger rod, such as an appropriately shaped recess as shown in FIG. 3, using an appropriate adhesive such as a cyanoacrylate. The accuracy of the strain gauge may be improved by carefully forming the adhesive bond.

The strain gauge 330 deforms in response to a force applied by a user to the proximal head 321 of the plunger rod as the plunger rod is deployed to perform an injection. The deformation of the strain gauge 330 induced by the applied force may cause an electrical resistance of the strain gauge to change and the change in resistance may be calibrated to determine a change in applied force as the plunger rod moves from its proximal position in the syringe barrel (not shown) prior to the injection being initiated to its end position in a distal portion of the barrel of the syringe, the end position being reached when a complete dose of the medicament has been administered to the patient. In this example, force measurements from the strain gauge 330 are relayed by electrical wiring to processing circuitry in the proximal head 321 of the plunger rod. The force measurement data from the strain gauge is analysed by the processing circuitry to determine when an end of injection has been reached without a requirement to measure a displacement of the plunger rod relative to the syringe barrel 104 using a displacement sensor such as a sensor that relies on reflection times to measure relative distance.

The sensitivity of the strain gauge 330 may vary depending on the applied user force. When administering an injection, user forces may be, for example, 10 Newtons or less. A strain gauge may be appropriately chosen to provide the best available sensitivity for this expected force range. For example, to account for overload conditions, a strain gauge may be selected such that it has good sensitivity in the range 0 to 20 Newtons. Stress, $\sigma$, is force, F, per cross sectional area, A, and strain, $\epsilon$, is a dimensionless quantity defined as extension per unit length. If E is an elastic modulus (also known as Young's modulus) of the strain gauge material, then the equations $E\epsilon=F/A=\sigma$ and $A=F/\sigma$ implies $\epsilon=\sigma/E$ can be used to determine appropriate strain gauge characteristics. Given the relatively low level of force being applied to the plunger rod by the user, the appropriate cross-sectional area under load may in some examples result in a small geometry of the order of a few mm in length and less than 1 mm in thickness to provide a sufficient level of strain (>1000$\mu\epsilon$).

Figure 4A:
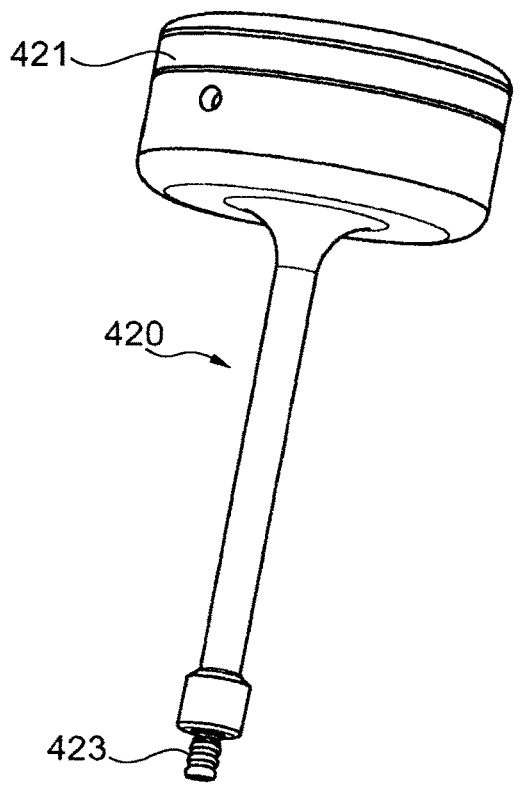
FIGS. 4a and 4b schematically illustrate a plunger rod implementing a force sensitive resistor (FSR) as a force sensor.
Figure 4B:
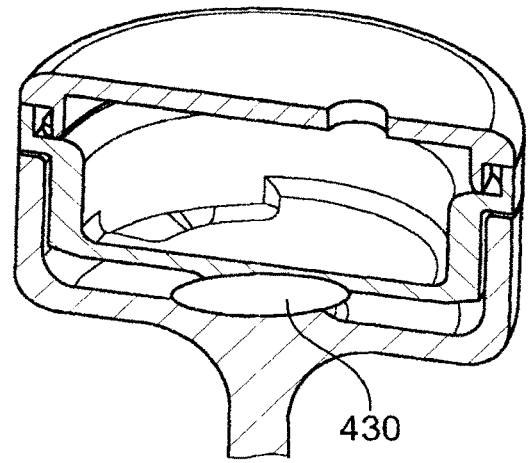

FIGS. 4a and 4b schematically illustrate a second example of a plunger rod, this time implementing a force sensitive resistor (FSR) 430 as a force sensor instead of a strain gauge. The FSR 430 may be conveniently located as shown in FIG. 4b, at the base of the proximal head 421, where the proximal head 421 meets an elongate portion of the plunger rod 420, although it may be located in a different position such as in the centre of the proximal head 421. The location of the FSR 430 and a configuration (shape and/or dimensions) of the proximal head 421 may be arranged to reduce any relative movement between the FSR 430 and a casing of the proximal head 421. Less relative movement implies less error in force measurements.

The configuration of the proximal head 421 may also be selected taking into account ergonomic aspects to compensate for potential poor user technique. For example, the configuration of the proximal head 421 may be chosen to reduce the likelihood of rocking or jamming of the plunger rod in the barrel of the syringe barrel 104 (see FIG. 1) as the plunger rod is performing an injection. The configuration may also be selected to reduce the likelihood of a user applying an off-axis force to the plunger rod. These proximal head configuration considerations may also apply to the examples of FIG. 3 or FIGS. 5a and 5b regardless of the particular type of force sensor employed. The FSR 430 of FIG. 4b may, in some examples, be a low-cost piezoresistive element.

In performing a calibration between a change in electrical resistance and applied force, the injection monitoring circuitry 126 (see FIG. 1) may include a temperature sensor to take into account temperature dependence of the calibration. An orientation sensor may be provided together with the strain gauge to allow the injection monitoring circuitry 126 to compensate for changes to the responsiveness of the strain gauge to force depending on orientation.

Figure 4C:
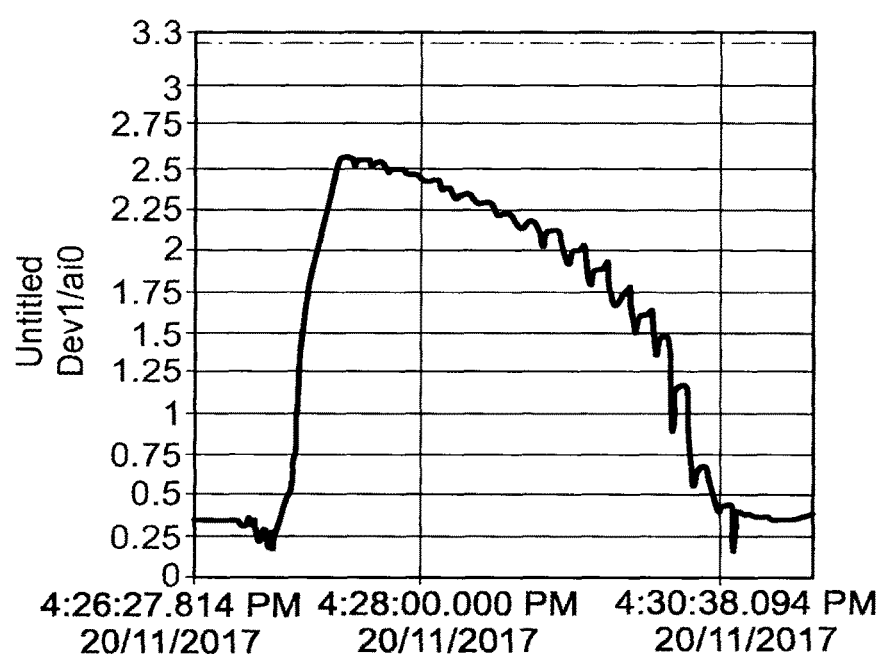
FIG. 4c is a graph schematically illustrating voltage against time values captured during a test of the force sensitive resistor in isolation from the plunger rod.

FIG. 4c is a graph schematically illustrating voltage against time during a test of the FSR 430 in isolation from the plunger rod 420 for force sensing capabilities. The graph of FIG. 4c can be compared with the graph of FIG. 5c for a MEMS force sensor.

Figure 4D:
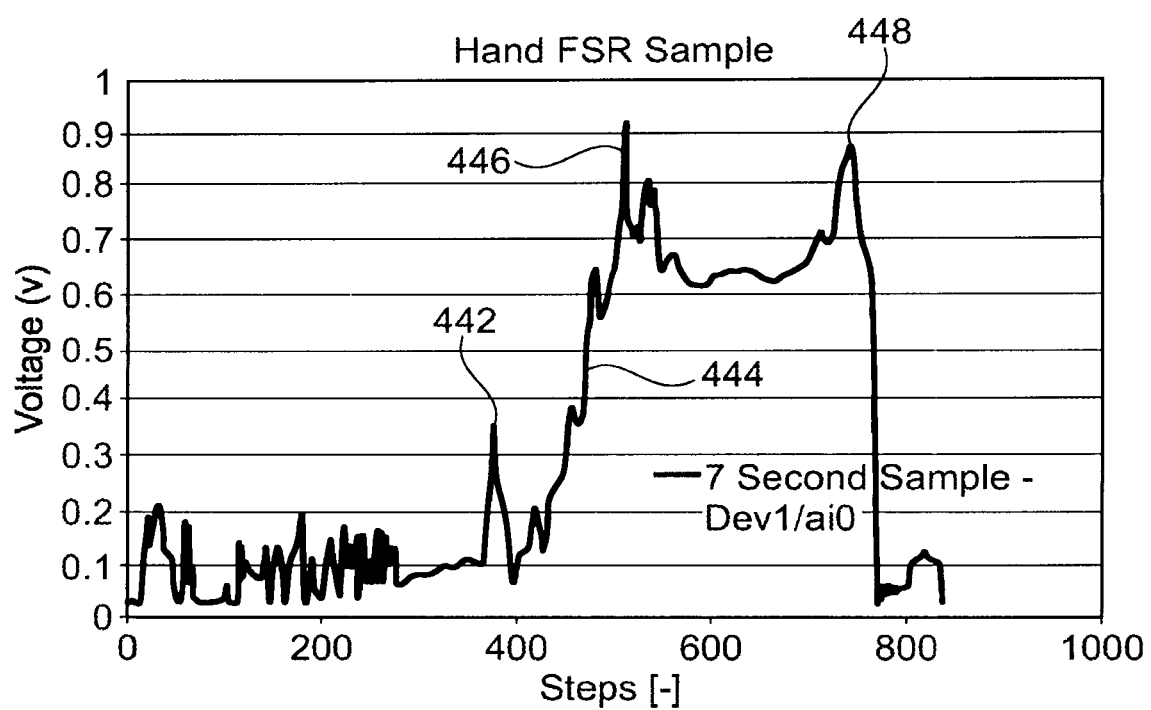
FIG. 4d is a graph of force against time schematically illustrating a user injecting into a silicone pad using an injection device incorporating the plunger rod of FIG. 4a incorporating the force sensitive resistor.

FIG. 4d is a graph of force against time schematically illustrating a user injecting into a silicone pad using an injection device incorporating the plunger rod 420 of FIG. 4a having the FSR 430 as a force sensor. The application of force by a user in an attempt to expel the medicament from the syringe barrel 104 (see FIG. 1) begins at a point 442 and the force measured by the FSR 430 then increases with a relatively steep gradient in the region 444, culminating at a data point 446 where friction between the plunger rod 420 (or resilient stopper thereof) and the barrel of the syringe barrel 104 has been overcome to allow movement of the plunger rod 420 towards the distal end of the syringe 102 (see FIG. 1) to expel the medicament. This is a "break loose" characteristic of the profile of FIG. 4d. The force detected is then relatively constant between point 446 and a point 448 at around timestep 800. This is a "glide" characteristic of the profile of FIG. 4d.

The data point 448 just before timestep 800 corresponds to a local peak in voltage that corresponds to the end of injection and representative of an "end-of-dose" characteristic of the voltage profile of FIG. 4d. After point 448, the sensed voltage drops off steeply to zero corresponding to the time immediately after completion of the injection when the plunger stopper has reached the distal end of the syringe barrel. The FIG. 4d graph shows just over 800 timesteps representing a seven second sample of force data. A duration of an injection event may vary for different users and for the same user between different injection events.

The graph of FIG. 4d also has non-zero voltage readings, indicating application of a force in the region between zero and four hundred timesteps, which corresponds to a user handing the injection device whilst inserting the plunger rod into a prefilled syringe and/or while inserting a needle of the injection device into an injection site before depressing the plunger rod. There is a readily distinguishable difference in the response of the FSR 430 (apparent from the force profile of FIG. 4d) to the user handling the plunger rod 420 during loading of the plunger rod into the syringe prior to the data point 422 and the response of the FSR 430 during a stroke of the plunger rod 420 when the proximal head 421 is pushed by the user to administer an injection, which corresponds to the voltage profile between data points 442 and 448. The voltage measurements of FIGS. 4c and 4d can be readily calibrated to convert the voltage measurements to force measurements. The voltage profile (variation of force sensor voltage with time) of FIG. 4d and also the corresponding force profile (variation of sensed force with time) are seen to show sufficient fidelity with time to extract the break-loose, the glide and the end of dose characteristic profiles. This demonstrates the suitability of the example plunger rods 421, 521 for characterisation of both qualitative and quantitative user performance in delivery of an injection using an injection device.

The plunger rod 420 incorporating the FSR 430 as shown in FIGS. 4a and 4b was found to have good resistance to interference relative to the plunger rod 320 incorporating the strain gauge 330 and had a comparatively better signal to noise ratio. The FSR 430 allows for simple integration into the injection monitoring circuitry of the proximal head 421 due to being deployable as a single element and the associated analog to digital (A/D) conversion is simple because it does not require multiplexing.

FIGS. 5a and 5b schematically illustrate an example plunger rod 520 having a set of MEMS force sensors. MEMS are micrometer-scale devices that integrate electrical and mechanical elements and having feature sizes ranging from micrometers to millimetres. MEMS are attractive for many applications because of their small size and weight, which allows systems to be miniaturized. In the FIG. 5b example, a set including three MEMS devices 532, 534, 536 are provided in the proximal head 521 of the plunger rod 520. In this example, the three MEMS devices are distributed at 120° intervals around the circumference of a central disc 538, the disc 538 being situated towards a distal portion of the proximal head 531. In other examples, different numbers of MEMS devices may be employed, although three devices have proved to be effective in measuring force applied by a user during an injection stroke.

The three MEMS devices 532, 534,536 may be connected in parallel. FIG. 5c schematically illustrates a voltage against time responsiveness for the MEMS force sensors 532, 534, 536 of FIG. 5b when deployed in a test rig to determine their effectiveness for force measurement. Comparison of the test force measurement graph of FIG. 5c for the MEMS force sensors with the corresponding graph of FIG. 4c for the FSR force sensor suggests that the FSR 430 has better resistance to interference and a better signal to noise ratio than the MEMS force sensors 532, 534, 536. However, the MEMS force sensors are convenient for high volume production, can provide good linearity of response, have good robustness and are relatively easy to assemble during a plunger rod production process.

In the example of FIG. 5b, function and performance of the MEMS sensors 532, 534, 536 may be fine-tuned by arranging the internal casing of the proximal head 521 to have a direct and rigid contact with the internal disc 538 to more evenly distribute the load between the plurality of sensors and to avoid all of the load being borne by a single MEMS sensor.

Figure 6A:
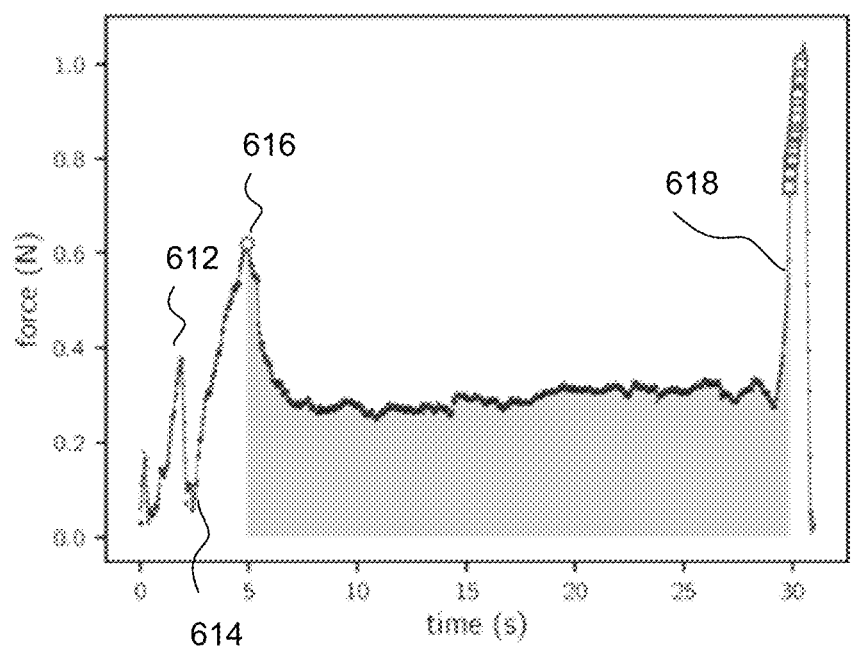
FIG. 6a is a graph of force in Newtons against time in seconds, the graph is a force profile schematically illustrating a first example of successful detection of a completion of dose corresponding to an end of injection for a "physics-based approach" to analysis of the force profile.

FIG. 6a is a graph of force in Newtons against time in seconds, the graph is a force profile schematically illustrating a first example of successful detection of a completion of dose corresponding to an end of injection for a "physics-based approach" to analysis of the force profile. The profile from zero to 5 s shows a first local peak 612 in detected force corresponding to the user handling the plunger rod 121 in preparation for an injection event. At a point 614, the user begins to apply force to the proximal head 121 to urge the plunger rod 120 through the barrel of the syringe 102 to administer the injection. There is then a gradient of progressively increasing force up to point 616 at 5 s where friction between the resilient stopper 114 and an interior wall of the syringe barrel 104 is being overcome.

Once the initial resistance due to friction has been overcome at around point 616, the detected force reduces from about 0.6N to approximately 0.3N whilst the plunger rod is in motion through the syringe barrel 104, performing expulsion of a medicament through the needle 112 into an injection site of a patient. Once delivery of a dose is almost complete at point 618, a rapid increase in the magnitude of the force applied by a user to the proximal head 121 from around 0.3N to approximately 1N is observed corresponding to the plunger rod reaching an end position in a distal portion of the barrel of the syringe during administration of the injection by the user. The user has a natural tendency to apply a relatively greater force to complete the injection event.

An area under the force profile between the points 616 and 618 may be calculated to determine a quantity denoted impulse. Impulse quantifies the overall effect of a force acting over time. It is conventionally given a symbol J and may be expressed in units of Newton-seconds. For a simple case of a constant force, $J=F*\Delta t$ where F is force in Newtons and t is time in seconds for which the force is applied. Calculation of impulse involves multiplying force by time, which is equivalent to determining an area under a force-time curve. A change in velocity of the plunger rod may be determined by dividing the impulse by the mass of the plunger rod 120 and an initial velocity at point 616 may be assumed to be zero. From the impulse, a displacement of the plunger rod in the syringe barrel may be deduced at one or more times in the 5 s to 30 s time interval to derive a displacement versus time graph from a force versus time graph without any direct measurement of displacement having to be made by a dedicated displacement sensor.

The integral under the force profile may also provide an estimate of energy expended or work performed during the injection event. A physics-based analysis of the force profile may include at least one of wavelet convolution or Fourier analysis to identify algorithmically at least the dosage complete point 618 which is deemed to correspond to the end of injection. Furthermore, a leading edge and a trailing edge of an injection stroke may be detected by determining gradients in different time portions of the force profile. A leading edge of an injection stroke may correspond to when a user has finished manipulating the proximal head 121 of the plunger rod 120 to engage it with the syringe barrel 104 and is in the initial stages of pushing the proximal head 121 of the plunger rod 120 towards a distal end of the syringe barrel 104 to administer a medicament to a patient through the needle 112. A trailing edge of an injection stroke may be a force profile towards the end of administration of an injection, once the resilient stopper 114 is at or close to a distal end of the syringe barrel and most or all of the medicament has been expelled from the syringe barrel 104 and delivered via the needle 112 to the injection site, whereupon a user begins to diminish force applied to the proximal head 121.

Fourier analysis may describe the process of breaking a function, such as a force profile, down into smaller components, the smaller components being trigonometric functions such as sinusoidal waves. The Fourier analysis may make the force profile easier to analyse.

Wavelet convolution uses a continuous wavelet transform to represent a signal such as the force profile of FIG. 6a. The technique has the ability to decompose complex information and patterns into elementary forms. A continuous wavelet transform is a convolution of an input data sequence (such as timestamped force measurements of a force profile) with a set of functions generated by a "mother wavelet". The convolution may be calculated using a Fast Fourier Transform algorithm. Wavelet transforms are known for use in image compression, acoustics processing and electrocardiogram (EEG) analysis, but according to the present technique, wavelet convolution may also be used to decompose a force profile from a plunger rod and representing variation of force with time during and close to an injection event to automatically identify when a complete dose of a medicament has been delivered, such as to identify the point 618 in FIG. 6a.

Whilst the features 612, 614, 616 and 618 may be readily distinguished by a trained human eye, the features may be more difficult to reliably identify algorithmically. Difficulties in identifying, for example, a complete dose of a medicament having been delivered may be exacerbated by variations in how individual users administer an injection and by noise in the signal that may vary between different injection events. For example, a user may start a medicament delivery stroke, pause to adjust their grip and then re-start the delivery stroke, leading to a discrepancy from an expected force profile such as the straightforward force profile of FIG. 6a. Other users may inadvertently administer an injection leaving some of the medicament in the barrel of the syringe so that a full dose is not received by the patient. Furthermore, it may be the case that a user has a poor grasp or an inconsistent grasp of the syringe 102 and plunger rod 120 due, for example, to arthritis or muscular sclerosis. This may cause the force profile to have anomalous features.

Figure 6B:
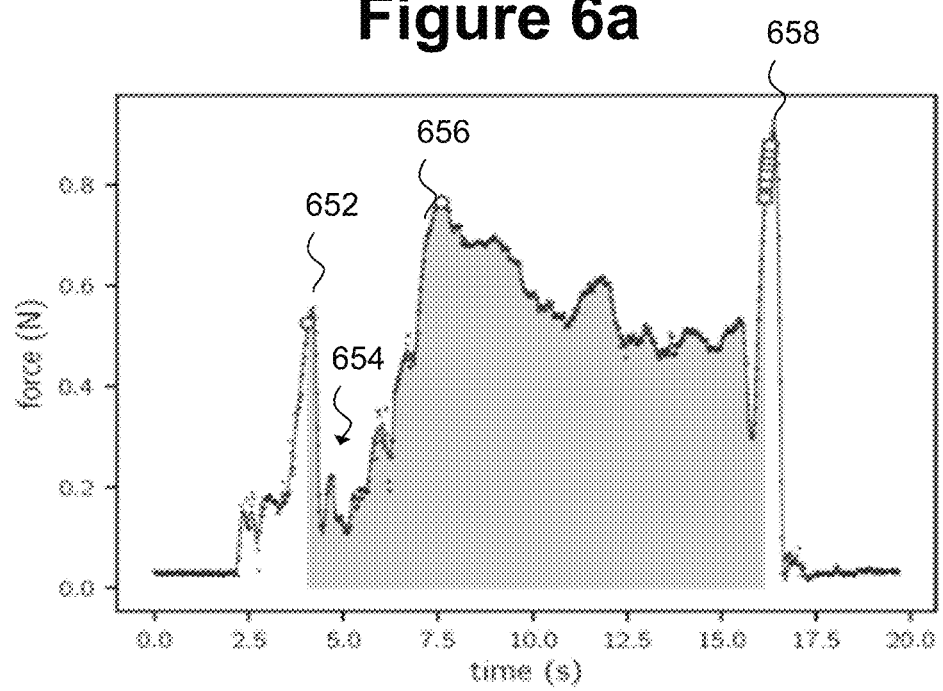
FIG. 6b is a graph of force in Newtons against time in seconds, the graph is a force profile schematically illustrating a second example of successful detection of a completion of dose corresponding to an end of injection for a physics-based approach to analysis of the force profile.

FIG. 6b is a graph of force in Newtons against time in seconds, the graph is a force profile schematically illustrating a second example of successful detection of a completion of dose corresponding to an end of injection for a physics-based approach to analysis of the force profile. The FIG. 6b force profile differs from the FIG. 6a profile in that after a peak 652 corresponding to an injection start, there is a local trough 654 in application of force detected by the injection monitoring circuitry of the proximal head 121 as, for example, a user adjusts their grip of the injection device, then a subsequent increase in force from less than 0.2N to more than 0.7N as the plunger rod 120 is pressed during a medicament delivery stroke and an end of injection where a full dose of medicament has been delivered is reached at a data point 658, when the force applied peaks at around 1N.

Successful algorithmic detection of the beginning of the injection stroke and the end of injection stroke was achieved with a physics-based approach both in the FIG. 6a example and in the FIG. 6b example, but it can be seen that the force profile is likely to vary considerably between different users and even for the same user at different times.

Figure 6C:
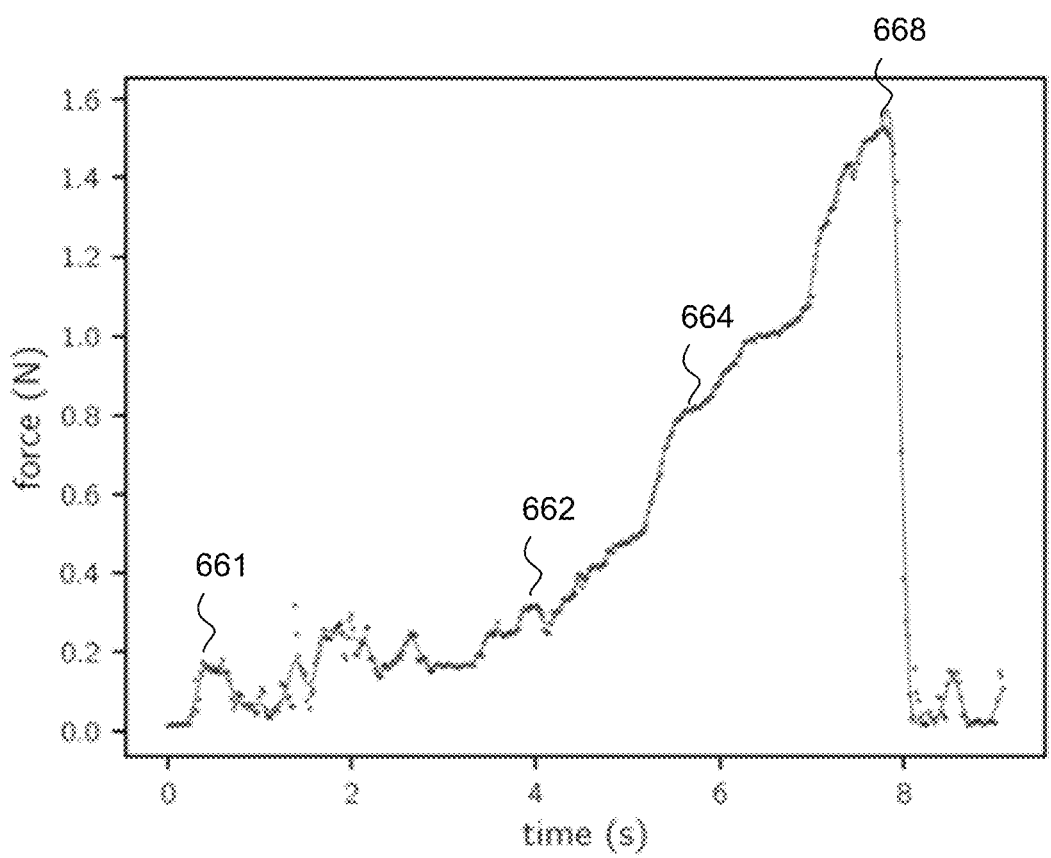
FIG. 6c is an example of a force profile which includes a graph of force in Newtons against time in seconds for an injection event for which the dose was not successfully completed.

FIG. 6c is an example of a force profile including a graph of force in Newtons against time in seconds for an injection event. The FIG. 6c force profile differs from the force profiles of FIG. 6a and FIG. 6b in that a start of the injection event is difficult to determine, even by visual inspection of the graph because there is no clear local peak analogous to the peak 616 of FIG. 6a or the peak 652 of FIG. 6b. Instead, there is a gradual increase in application of force from data point 661 at about half a second into the force profile where the force is less than 0.2N, rising gradually (with many local minima and maxima) to around 0.3N at data point 662 just over 4 seconds in. Then there is a steeper gradient between data point 662 and a data point 664 at around 5.5 s in where the force reaches approximately 0.8N. There is then a further relatively steep gradient from a data point 664 to a data point 668 at which the force reaches its maximum magnitude of around 1.5 N at 8 s. before sharply decreasing to zero within a small fraction of a second.

Although the human eye might conclude that the data point 668 of FIG. 6C corresponds to an end of injection where a complete dose has been delivered, detection of this end of injection event proved unsuccessful with a physics-based approach. However, overall in trial applications of the physics-based approach on multiple force profiles for a number of different users, accuracy was found to be around 60%. Further fine-tuning could improve this accuracy.

An alternative approach to the "physics-based approach" of analysing the force profiles for injection events using integration to determine displacement and using decomposition via Fourier analysis and/or wavelet convolution, is to use a statistical machine-learning approach. One advantage of the physics-based approach is that the numerical analysis is relatively low complexity and can be readily performed by a low-power embedded device provided on the plunger rod or elsewhere on the syringe. The present technique encompasses both the physics-based approach and the machine-learning approach.

One challenge in accurately determining a complete dose delivery during an injection event is the range of noise that is typically present due to, for example, a user handling the syringe to push the needle 112 (see FIG. 1) into a patient's skin or a user adjusting their grasp on the syringe and plunger mid-injection. The machine learning approach provides a convenient and reliable way of improving an accuracy of the dose complete or incomplete determination and can be more resilient to noise in the force profiles. The machine learning approach is of moderate complexity relative to the physics-based approach but is still simple enough to allow the algorithms to be executed on an embedded device on the plunger rod and/or on the syringe.

A further approach also encompassed by the present technique is of higher complexity and may involve neural networks. Neural network implementations are likely to require a processor such as a graphics processing unit (GPU) or a tensor processing unit (TPU), which is a custom-built integrated circuit developed specifically for machine learning. Furthermore, whereas around five hundred successful and five hundred unsuccessful injection force profiles for up to one hundred users have been found to be adequate to train a machine learning model and to select a deployment model with at least around 80% accuracy, tens or hundreds of thousands of example force profiles may be appropriate to achieve acceptable accuracy for a neural network implementation.

Machine learning approaches construct algorithms that can learn from and make predictions on data. In particular, according to the present technique, a machine learning model is developed using a set of force profiles for a plurality of different users with the force profiles having been categorised into successful injection events in which a complete dose has been delivered to patient and unsuccessful injection events involving incomplete delivery of a dose of a medicament to patient.

Figure 7:
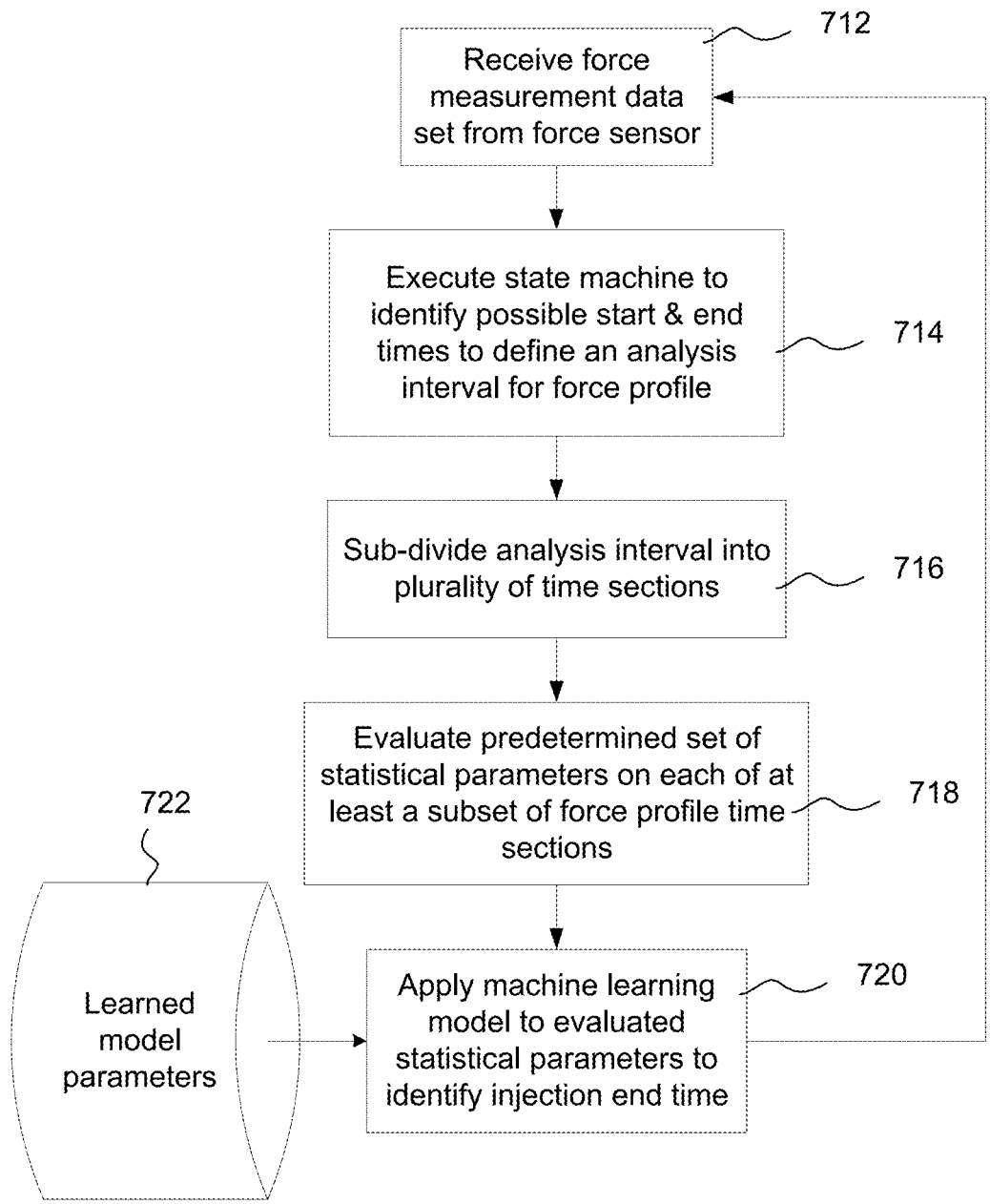
FIG. 7 is a flowchart schematically illustrating a machine learning approach to determining an end of injection corresponding to successful delivery of a complete dosage.

FIG. 7 is a flowchart schematically illustrating an algorithm that applies machine learning to determine an end of injection corresponding to a complete dosage having been delivered to a patient (and thus a successful injection event). Processing associated with the method of the flowchart of FIG. 7 may be performed entirely on processing circuitry 258 of the plunger rod, entirely on processing circuitry of the user device 150, entirely on processing hardware of the cloud platform 160, or alternatively, the machine learning processing may be distributed across two or more of the plunger rod processing hardware 258, the user device 150 and the cloud platform 160 (see FIG. 1).

The method begins at processing element 712 where a set of force measurement data captured during an injection event is received, for example, from the force sensors 256a, b, c of the injection monitoring circuitry 254 of the plunger rod 220. Next, at process element 714, a state machine is executed on the force profile data to identify possible start and end times for an injection event to define an analysis interval for the force profile. The start time for analysis may correspond to time prior to the user initiating an injection stroke and similarly the end time for analysis may correspond to a time after the end of injection when the dose is complete. For example, the start time for analysis may begin when circuitry in the proximal head 121 of the plunger rod 120 is switched on, which may be seconds or minutes before the user initiates the injection stroke. The end time for analysis after the end of the injection may be, for example, a few seconds or more after a possible end of injection has been detected. The analysis interval determined by the state machine is selected to derive as much information as possible in order to accurately determine whether an injection stroke corresponds to a successful injection in which the complete dose has been delivered to the patient or an unsuccessful injection in which an incomplete dose has been delivered to the patient, as explained hereinbelow. Use of a state machine to identify the start and end times for the machine learning analysis makes the process more efficient by reducing the number of force data measurements that are subject to the numerically intensive machine learning analysis.

Figure 9A:
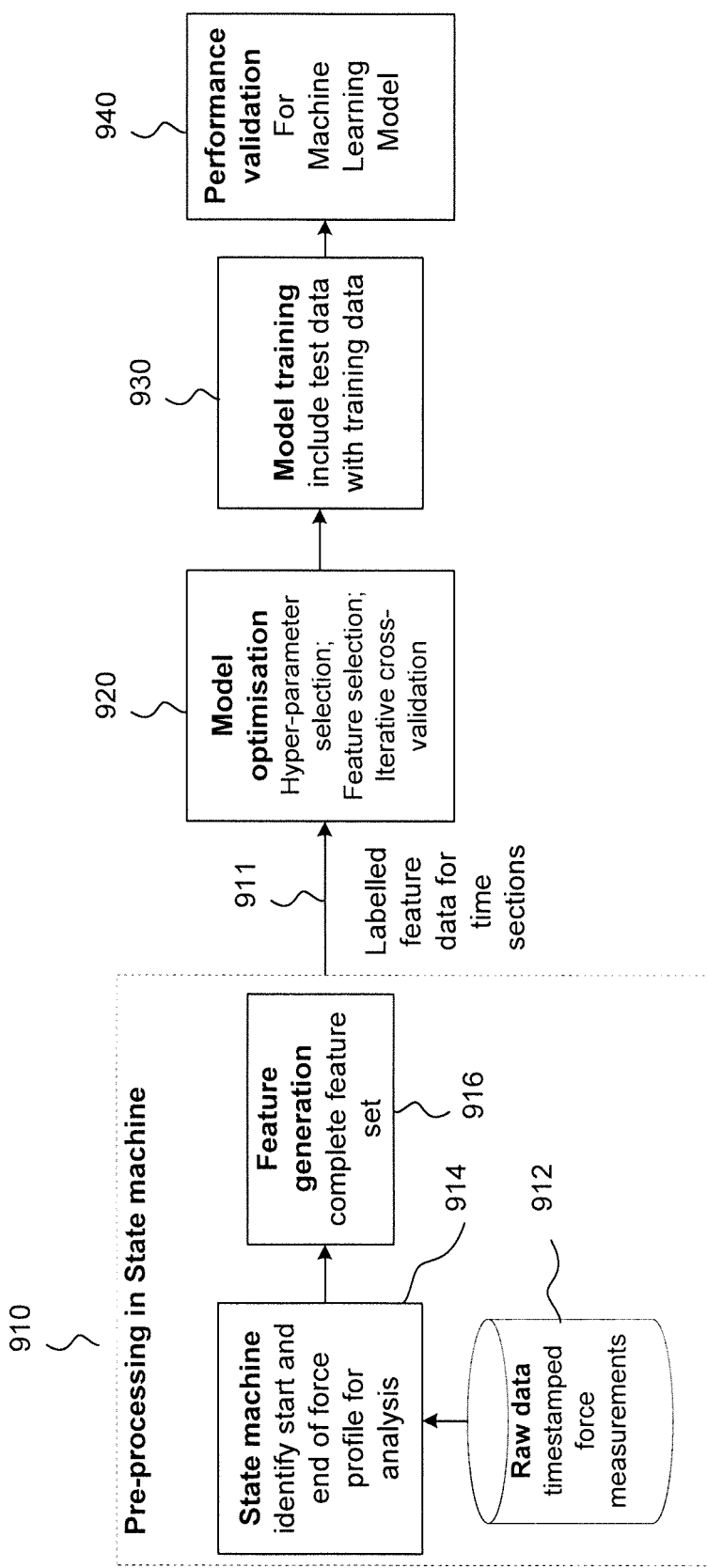
FIG. 9a schematically illustrates a process flow for machine learning model development for implementation in an injection device.

After the state machine has identified possible start and end times of the force profile, the process proceeds to process element 716 with the identified analysis interval subdivided into a plurality of time sections. For example, a number of time sections in the range between five and twenty time-sections may be conveniently used. Then at process element 718, for each of the time sections, a predetermined set of statistical parameters is evaluated for the force profile. The particular statistical parameters selected for evaluation may be determined based on a set of parameters found to provide the most effective model during training of a machine learning algorithm on a labelled data set. FIG. 9a described below illustrates the machine learning development process. Examples of statistical parameters may be evaluated at process element 718 include, for example: injection duration; mean force across all time intervals and standard deviation across all time intervals.

At process element 720, a previously determined machine learning model is applied to an output of the state machine to make a decision on whether or not a successful injection has been performed involving a complete dose delivery. Process element 720 depends on an input data set 722 corresponding to a set of learned model parameters determined from training and validation data sets, to the extent that the deployed machine learning model was selected based on "learned model parameters" established during the machine learning development.

Although the state machine may identify possible start and end injection times at process element 714, these times may be identifiable in a force profile without a complete dose of medication having been delivered. For example, an injection stroke may end before the resilient stopper has been depressed to the end of the syringe barrel, resulting in an unsuccessful injection due to an under-dose. The machine learning model applied at process element 720 allows many and various features of a force profile to be taken into account to make a prediction as to whether or not a complete dose of the medicament has been delivered by the end of the injection.

In principle, this determination could be made in some cases by judgement of a human eye of a highly trained user, but the machine learning model is capable of taking into account variability in how users apply pressure during the injection delivery stroke and to take into account variation between different injection devices at least matching the performance of an expert human user but automating the process allowing feedback to be provided to the average user that might otherwise be available only via expert analysis. The use of the state machine as a precursor to the machine learning model simplifies the prediction process, making it more efficient to perform.

Figure 8:
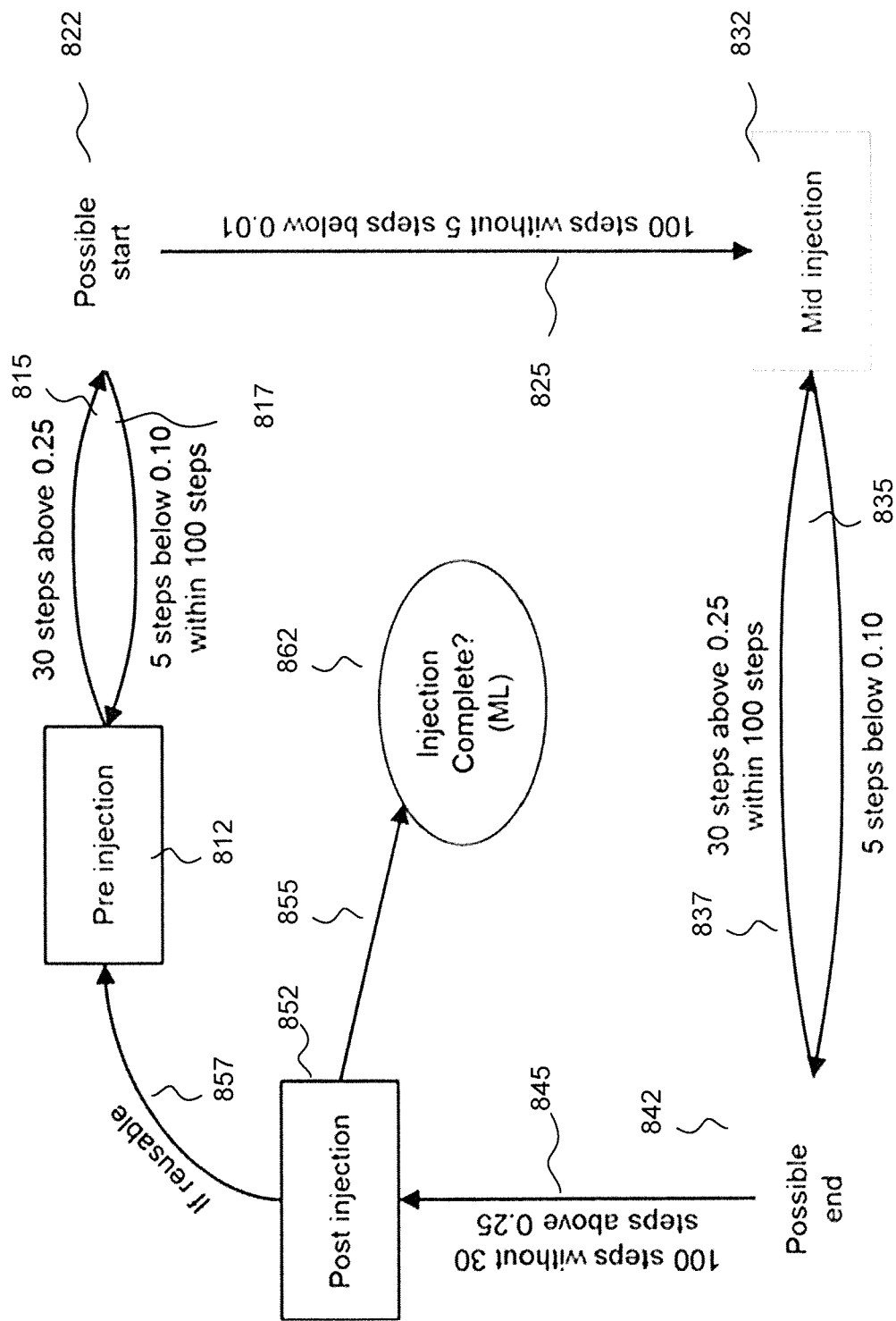
FIG. 8 is a flow diagram schematically illustrating transitions between a plurality of different injection states as determined by a state machine.

FIG. 8 is a flow diagram schematically illustrating transitions between a plurality of injection states as determined by a state machine. As illustrated in the flowchart of FIG. 7, the state machine may be used as a precursor to a machine learning algorithm. In particular, the state machine may be used to identify a possible start and possible end time from force profile data gathered during an injection event. In FIG. 8 the "steps" refer to time steps which may be for example time steps including a fraction of a second such as 1/30 of a second, but different magnitudes of time step may be used. The magnitude values refer to absolute voltage values, but the present technique is not limited to this and relative voltage increases or relative force values may be used based on output of the force sensor(s). The voltage from a force sensor 124 (see FIG. 1) in the proximal head of the plunger rod is used in this example to provide an indication of force. Any measurement parameter that is proportional to the applied force may be used and voltage is just one example. Force values in Newtons obtained from a force sensor in the plunger rod could alternatively be used.

State 812 corresponds to a pre-injection state in which the user may be handling injection device, for example, involving applying some force to the proximal head 121 (see FIG. 1) of the plunger rod whilst inserting the needle into an injection site. Thus, in a pre-injection state 812, there may be non-zero force readings registered by the force sensor. A transition from the pre-injection state 812 to a possible injection start state 822 is determined upon detection of a predetermined number of time steps above a certain threshold magnitude. In this example, the transition depends on evaluation of the condition 815 involving detection of at least thirty time steps above a voltage magnitude of 0.25V. The threshold voltage of 0.25V is sufficient in this example to deduce that user is applying force to the proximal head of the plunger rod to overcome friction between the resilient stopper and the inside of the syringe barrel. The level of force required may vary for different syringes depending on, for example an amount of lubricant such as silicon that has been deposited on an inner wall of the syringe barrel 104.

Even once thirty time steps above 0.25V have been detected at 815 and the possible start state 822 has been established, the system may revert to the pre-injection state 812 in the event that a predetermined number of steps below a minimum threshold voltage is detected within a predetermined time interval corresponding to the condition 817. In particular, if five steps below 0.1 V are detected at 817 within one hundred time steps, then reversion to the pre-injection state 812 is initiated. This determination is based on it being unlikely that during a successful injection there will be more than five time steps below the low force value corresponding to 0.1V, because this force would likely be inadequate to move the plunger rod to displace it within the syringe barrel. The magnitude of this threshold value may be implementation-dependent and may thus be user configurable.

A transition from a pre-injection state to an injection start state may be determined according to the present technique depending on detecting a configurable predetermined number of timesteps for which the measured voltage (or force) is above a predetermined injection-start threshold within a given time window. The voltage (force) measurements above the threshold to trigger the injection start state identification may be constrained to be contiguous in time in some examples, but may alternatively be non-contiguous in time provided the number of measurements above the injection-start threshold is within the given time window. The voltage (force indicating measurement) corresponding to the injection-start threshold may be selected such that it corresponds to a higher value than a typical force applied by a user when handling the plunger rod prior to applying force to depress the plunger rod into the syringe barrel to deliver the medicament.

A transition from the injection start state to a mid-injection state may be determined according to the present technique depending on detecting a configurable predetermined number of timesteps for which the measured voltage (or force) remains above a predetermined mid-injection threshold within a given time window, but optionally allowing for a relatively small number of timesteps for which the measured voltage may transiently dip below the configured mid-injection threshold. The mid-injection threshold may be the same as the pre-injection threshold in some examples or may alternatively differ from it. A user may initially apply a higher force to overcome friction against movement of the resilient stopper of the plunger rod in the syringe barrel when starting an injection stroke and may subsequently reduce the applied force, so in some examples the mid-injection threshold may be set to take account of this. However, it will be appreciated that a single threshold force magnitude could be applied to both detection of injection start and to detecting a mid-injection state. Similarly, the given time windows within which the injection start and mid-injection state determinations are made may have the same duration or may alternatively differ in duration. In the example of FIG. 8, both windows have the same duration of 100 time steps.

From the possible start state 822, a transition may be made to a mid-injection state 832 if a condition 825 is satisfied, whereby one hundred time steps are detected without detecting five time steps below a voltage of 0.01 V. Although one might consider that it would be sufficient only to detect one hundred time steps above 0.25V, it has been noted empirically that there can be a short period in a force profile where a user apparently applies close to the negligible force to the proximal head the plunger rod corresponding to expelling a small bubble of gas typically present within the medicament through the needle 112. The gas bubble gives a temporary reduction in application of force that looks like an injection stroke might have stopped. This is because the medicament is likely to be in liquid form and this liquid has a high viscosity relative to a viscosity of the gas bubble. The gas bubble thus needs only negligible force to expel it from the syringe. However, after the small gas bubble has been expelled, the application of force is likely to rise in magnitude again above 0.25V.

If the system is in the mid-injection state 832, a determination may be made as to whether or not a transition has been reached resulting in a possible end injection state. The system transitions from the mid-injection state 832 to the possible end injection state 842, if starting from the mid-injection state 832, five or more steps below 0.1V are detected. This is because during delivery of a medicament during a successful injection there is unlikely to be a reduction in force below a reading of 0.1V for a duration of longer than five steps. However, even if the possible end state 842 is reached, the system may revert to the mid-injection state 832 if thirty steps above a value of 0.25V are subsequently detected within one hundred times steps. This state change from end of injection 842 to mid-injection 832 is likely to occur if the end of injection has been incorrectly identified due to, for example, a temporary reduction in applied force due to a subtle change of the user's hand position mid-stroke when performing an injection. It has been found that such subtle changes in grip position can sometimes be expected when the plunger rod has completed approximately 75% of a full injection stroke within the syringe barrel.

When in the possible end state 842, a transition may be made to a post injection state 852 in the event that an analysis determines from the force profile that a condition 845 has been satisfied, whereby at least one hundred time steps have elapsed without at least thirty steps above 0.25 Volts.

If the injection device is reusable, then a transition from the post injection state 852 to the pre-injection state 812 may be implemented.

A transition from a mid-injection state to an injection end state may be determined according to the present technique depending on detecting a configurable predetermined number of timesteps for which the measured voltage (or force) is below a predetermined injection-end threshold within a given time window. As in the FIG. 8 example, the measurements that fall below the force threshold are not necessarily contiguous in time, but some examples may use a constraint whereby the force measurements below the threshold are contiguous in time. The given time window used to assess whether or not an end of injection state has been reached may be the same as or may differ from one or both of the time window used to determine the start of injection state and the time window used to determine the mid-injection state.

Although specific different voltage (corresponding also to force) thresholds have been specified in the state diagram of FIG. 8 to trigger transitions between different injecting states, alternative thresholds may be defined. Similarly, different magnitudes of timesteps may be defined in different examples. Although voltage magnitude is used as a force measurement in the FIG. 8 example, this is non-limiting.

FIG. 9a schematically illustrates a process flow for machine learning model development for implementation in an injection device. Some pre-processing is performed in a state machine as represented by process element 910. The state machine operates on raw data from the force sensor(s) including a force profile of timestamped force measurements 912. The raw data 912 in this case represents force profiles where an outcome of the associated injection events is known. Thus, for example, the raw data 912 may include force profiles for five hundred successful injections and for five hundred unsuccessful injections for up to one hundred different users. The raw data 912 has labels for each profile indicating at least whether or not the respective profile corresponds to a successful injection or an unsuccessful injection.

The raw data 912 should ideally contain carefully sampled data, spanning various classes that the model is likely to face when used in the real world. According to the present technique, the raw data may include examples of different gradients of force profiles representing beginning and end of injection and different mid-injection force versus time profiles and different pre-injection and post-injection force measurement patterns for each of the successful injection and unsuccessful injection categories. Different injection durations may also be included in the model development. To generate a machine learning model, the raw dataset 912 can be split into training, validation and test datasets. Some machine learning models need more data to train upon than others this can influence how a dataset is divided up into the three components. Models with very few "hyper-parameters" are easier to validate and tune so the size of the validation set can be reduced in such models At process element 914, a state machine, such as the state machine schematically illustrated by FIG. 8, is applied to the raw data to identify a start point and end point within the force profile. The state machine may divide the force profile data into time intervals (or equivalently time steps). The state machine time intervals may differ from the time-separation of successive force measurement values in the raw data and are likely to be longer than the force sampling period. Once the state machine has determined start and end points for an injection event at process element 914, the state machine performs, at process element 916, statistical analysis of the raw data to determine a complete feature set for a predetermined list of features.

The full set of features generated at element 916 is configurable by a user, but may include, for example: injection duration; mean force across all time intervals and standard deviation across all time intervals; skew (3rd statistical moment) across all time intervals; kurtosis (4th statistical moment) across all time intervals; data quartiles: minimum, 25th percentile, median, 75th percentile, maximum; mean of at least a non-zero subset of the plurality of time sections; standard deviation of at least a non-zero subset of the plurality of time sections. Some alternative examples may use at least one of statistical moment and descriptors of data before the start and after the end and further descriptors of each time interval in the full feature set. Thus, the full feature set may include statistical measures, determined globally between the start point and the end point and may include statistical measures evaluated selectively for a contiguous or for a non-contiguous subset of the plurality of time intervals into which the state machine divides up the force data. Force measurements prior to the start point and/or after the end point identified by the state machine may also be used as part of the complete feature set in some examples.

Once pre-processing in the state machine represented by unit 910 has been performed, an output 911 of the pre-processing performed by the state machine is "labelled" (or tagged) feature data for the state machine time intervals. The raw data 912 in this example is not supplied to a model optimisation unit 920, but the labelled feature data 911 is supplied to the next stage. The model optimisation unit 920 executes an iterative process used to identify an appropriate machine learning model that is capable of reliably predicting an outcome of an injection event as a successful injection event, where the end of injection is reached with a complete dose of the medicament having been delivered, or an unsuccessful injection event where there may be no definitive start or end of injection or where the statistical parameters indicate that the appropriate medicament dosage has not been delivered.

During the model development illustrated by FIG. 9a, a mathematical model is derived from the labelled feature data 911 and once developed, the model may be used to analyse previously unseen force profile data to make a prediction on whether or not an injection event included in the new force profile represents a successful injection event or an unsuccessful injection event. The labels may include, for example, injection start, injection end and successful injection. The data used to build a deployed machine learning model may come from multiple datasets used in different stages of creation of the machine learning model.

For example, in the model optimisation unit 920, a candidate machine learning model may be initially fitted to a training dataset, which would represent a number of successful injection events and unsuccessful injection events for different users. The training data set in this case may be a subset of the labelled feature data 911. A candidate machine learning model may be trained on the training dataset using a supervised learning method such as, for example, Support Vector Classification (SVC) or boosted gradient trees or neural networks.

SVC is a supervised learning algorithm that takes labelled training data as input and outputs an optimal hyperplane that categorises new examples. In two-dimensional space the hyperplane is a line dividing a plane in two parts such that two different classes of data may lie on either side of the line.

The Boosted Gradient Trees technique produces a prediction model in the form of an ensemble of weak prediction models, typically decision trees. It builds the model in a stage-wise manner like other boosting methods do, combining weak "learners" into a single strong learner in an iterative way. The method involves optimization of an arbitrary differentiable loss function.

Alternative machine learning models, such as SVC and Boosted Gradient Tree, are run with the training dataset and each candidate model produces a result which is then compared with a target results (dose complete or dose incomplete) defined by the corresponding label. A particular machine learning model is selected from the plurality of candidate models based on an accuracy of prediction, or equivalently, based on a goodness of fit of the model to the training data.

The selected machine learning model is then used to predict injection outcomes (and possibly other parameters) for a second dataset denoted a validation dataset. The validation dataset is intended to provide an unbiased evaluation of a model "fit" on the training dataset while tuning the model's hyper-parameters. A hyper-parameter may be a parameter whose value is set before the training phase begins, or a range provided over which successive training runs are performed to determine an appropriate (perceived optimum) setting. Example hyper-parameters are "gamma" for SVM models using a Radial Basis Function kernel or "minimum child weight" for Boosted Gradient Trees. The validation dataset may be used to detect undesirable over-fitting of a machine learning model to the training dataset by stopping training when an error on the validation dataset increases.

In a model training unit 930, which receives an output of the model optimisation unit 920, a test dataset is used to provide an unbiased evaluation of the final model fit on a training dataset. The test dataset is only used once the machine learning model has been completely trained using the training dataset and validation dataset by the model optimisation unit 920 and the test dataset is generally used to evaluate competing machine learning models for accuracy.

A process called cross-validation may be used to avoid over-fitting of the machine learning model to the training data during machine learning model development. Cross validation may span the model optimisation 920, the model training 930 and the performance validation 940 units of FIG. 9a. The cross validation may involve splitting the model development dataset, in this case corresponding to the labelled feature data 911, into a training set and a validation set (for example, in the ratio 80:20). Multi-fold cross validation may then be performed. In one example, five-fold cross validation may be performed including sub-dividing the training data set into five "bins", and in a first iteration using bins two to five as training data and bin one as test data. In the next iteration, training may be performed using bins one, three, four and five as training data and bin two as test data, and so on such that each of the five bins is used as test data in one of the five iterations. The validation data is held back until the model training and hyperparameter optimisation is complete. Once complete, the validation data may then be used to determine a final accuracy statistic. Such cross validation may avoid over fitting and thus make the deployed machine learning model more accurate.

In alternative examples to the FIG. 9a example, the state machine pre-processing 910 is omitted, in which case the cross-validation may be performed on the raw data 912 rather than the labelled feature data 911.

Figure 9B:
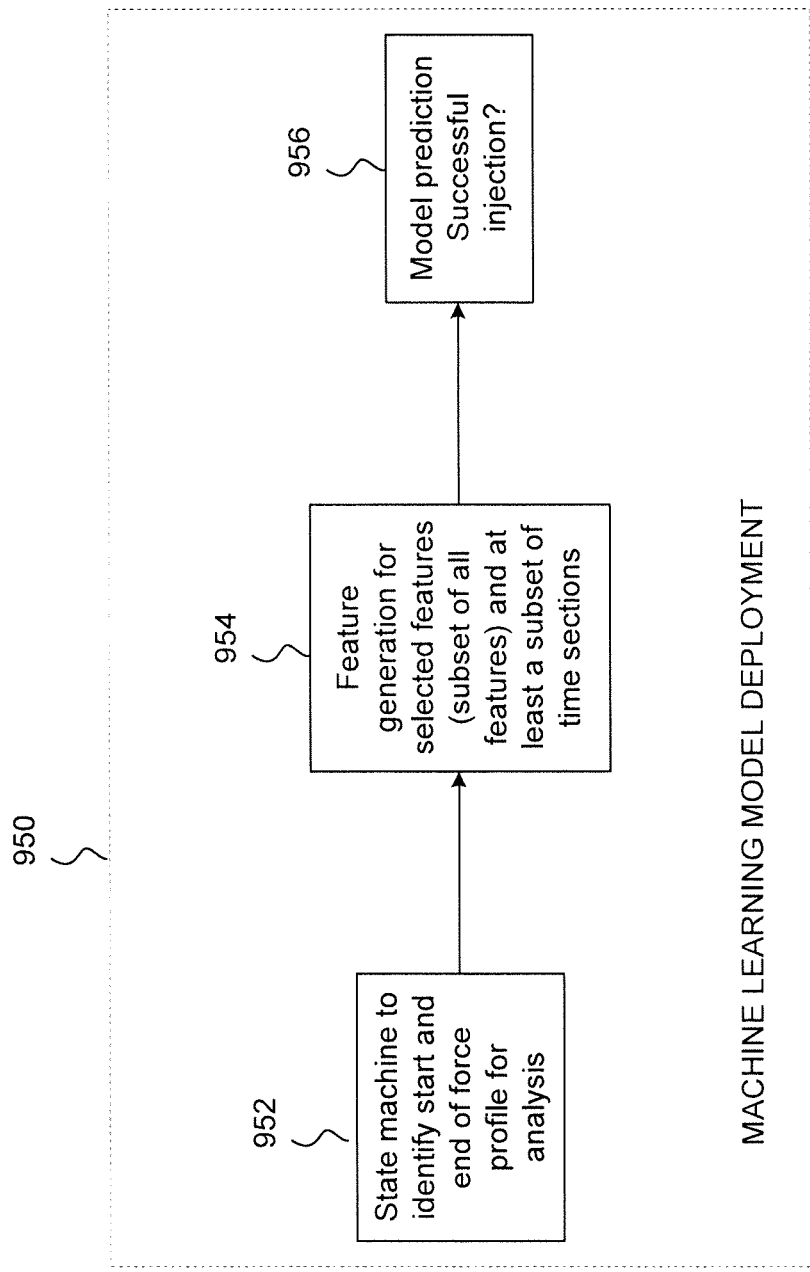
FIG. 9b schematically illustrates a sequence of processing units to implement deployment of a selected machine learning model, the selection having been made using the FIG. 9a process flow.

FIG. 9b schematically illustrates a sequence 950 of processing units to implement deployment of a selected machine learning model. The machine learning model deployment has a deployment state machine 952 that operates on force profile data dynamically generated by injection devices when deployed by users. Contrast this with the state machine of process unit 914 of FIG. 9a that operates on labelled model training data relating to validated injection outcomes. Output of the deployment state machine 952, which identifies a start and an end point is output to a selected feature generation unit 954 that determines values of statistical parameters for at least a subset of the state model time intervals, the statistical parameters being fewer in number than the complete feature set calculated in the feature generation unit 916 of FIG. 9a.

For example, the complete feature used in the machine learning model development of FIG. 9a may include a total of thirty features whereas the selected features subset may include around fifteen of the thirty features determined in the deployed model to be the most accurate predictors of a target outcome. The selected subset of features may include at least one of: parameters evaluated for particular time intervals and parameters evaluated to span multiple time intervals of a corresponding force profile. In the model deployment process, a model prediction unit makes a prediction based on the model as to whether or not the force profile has characteristics of a successful injection event. Further predictions may also be made such as an injection start and end time and an injection duration.

Figure 10A:
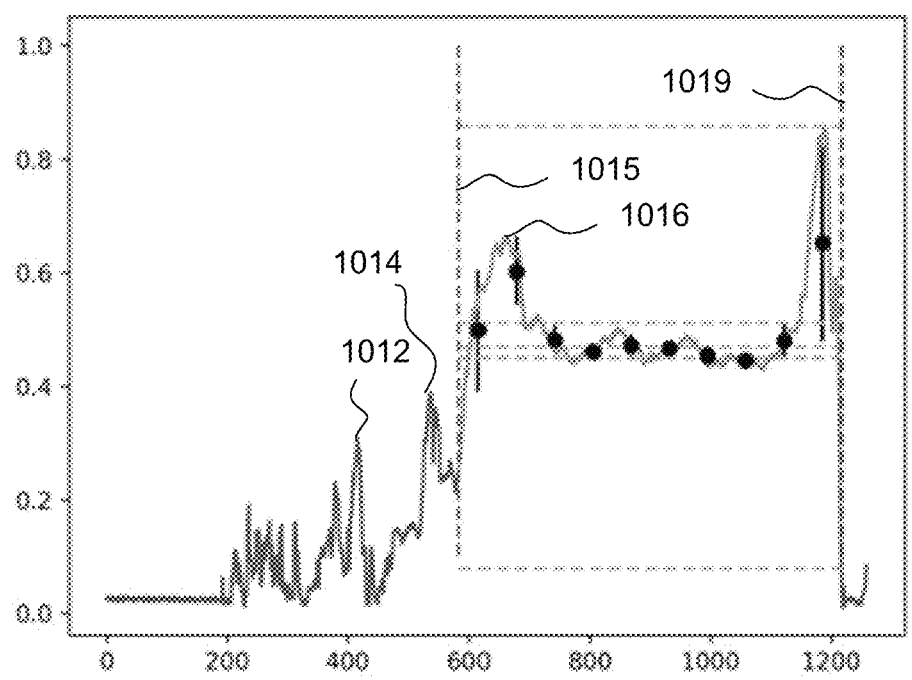
FIGS. 10a and 10b are graphs of normalized force against time representing force profiles for which the machine learning algorithm according to the present technique predicted a successful injection.
Figure 10B:
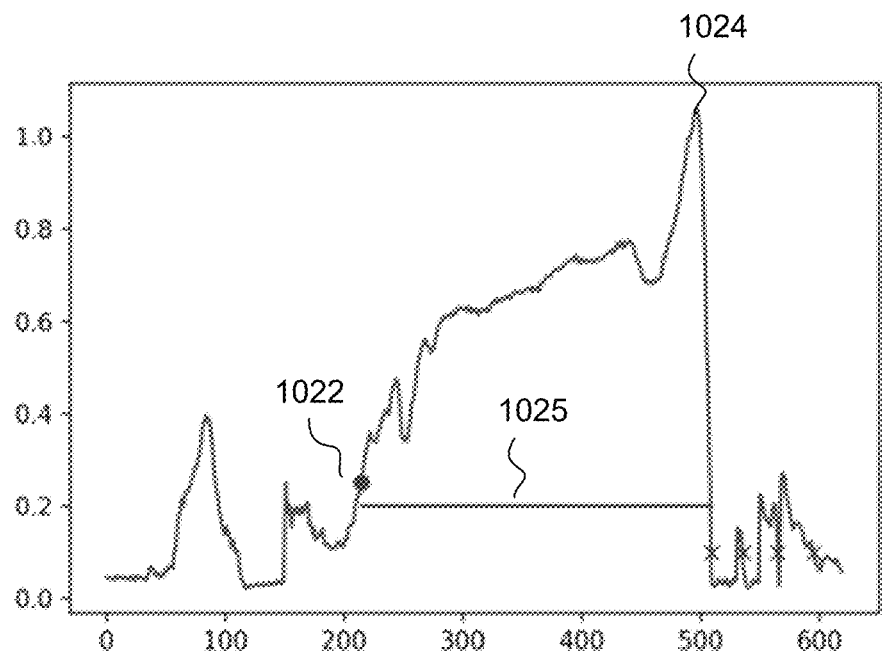

FIGS. 10a and 10b are graphs of normalized force against time representing force profiles for which the machine learning algorithm according to the present technique predicted a successful injection (meaning that a complete medicament dose was delivered). FIG. 10a has a period between two hundred and six hundred time units corresponding to noisy force data in a pre-injection period. This may correspond, for example, to the user pushing the needle into skin at a target injection site. Viewing the data by eye, any one of the local peaks 1012, 1014 or 1016 between four hundred and six hundred time units could potentially correspond to an injection start event. However, the state machine combined with the machine learning algorithm identify an injection start at a line 1015, an injection end at a line 1019 and an injection duration spanning between these two lines, that is between about six hundred and about twelve hundred time steps, giving a total duration of about six hundred time steps.

The successful injection event force profile of FIG. 10b has a total duration of only around six hundred time steps in comparison to the twelve hundred time steps of the FIG. 10a example. Further differences between the two force profiles are that the pre-injection period before a data point 1022 in FIG. 10b has relatively fewer local peaks than the force profile of FIG. 10a. Furthermore, a post-injection period after the injection end peak 1024 of FIG. 10b shows several peaks of up to about a quarter of the magnitude of the injection end force. The deployed machine learning algorithm predicts an injection duration represented by a line 1025 representing about three hundred time units.

Figure 10C:
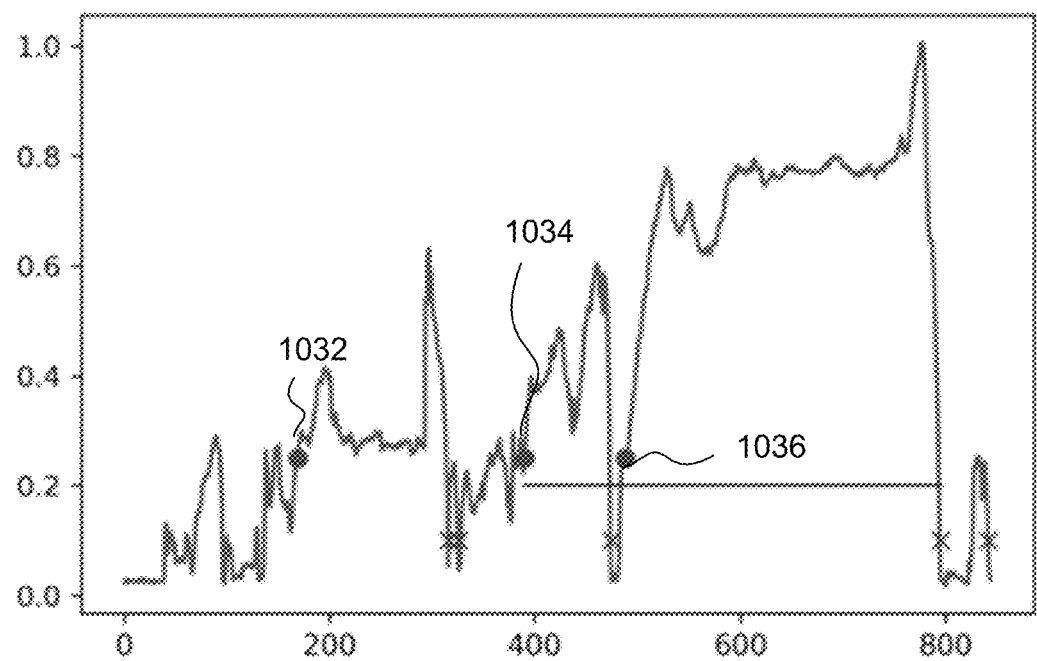
FIG. 10c is an example force profile in which there are three alternative potential injection start points.

FIG. 10c is an example force profile in which there are three alternative potential injection start points 1032, 0034 and 1036 at about two hundred, about four hundred and about six hundred time steps respectively. This force profile is associated with a predicted successful injection but with user guidance to "keep pushing" at about half way through the injection stroke.

Figure 10D:
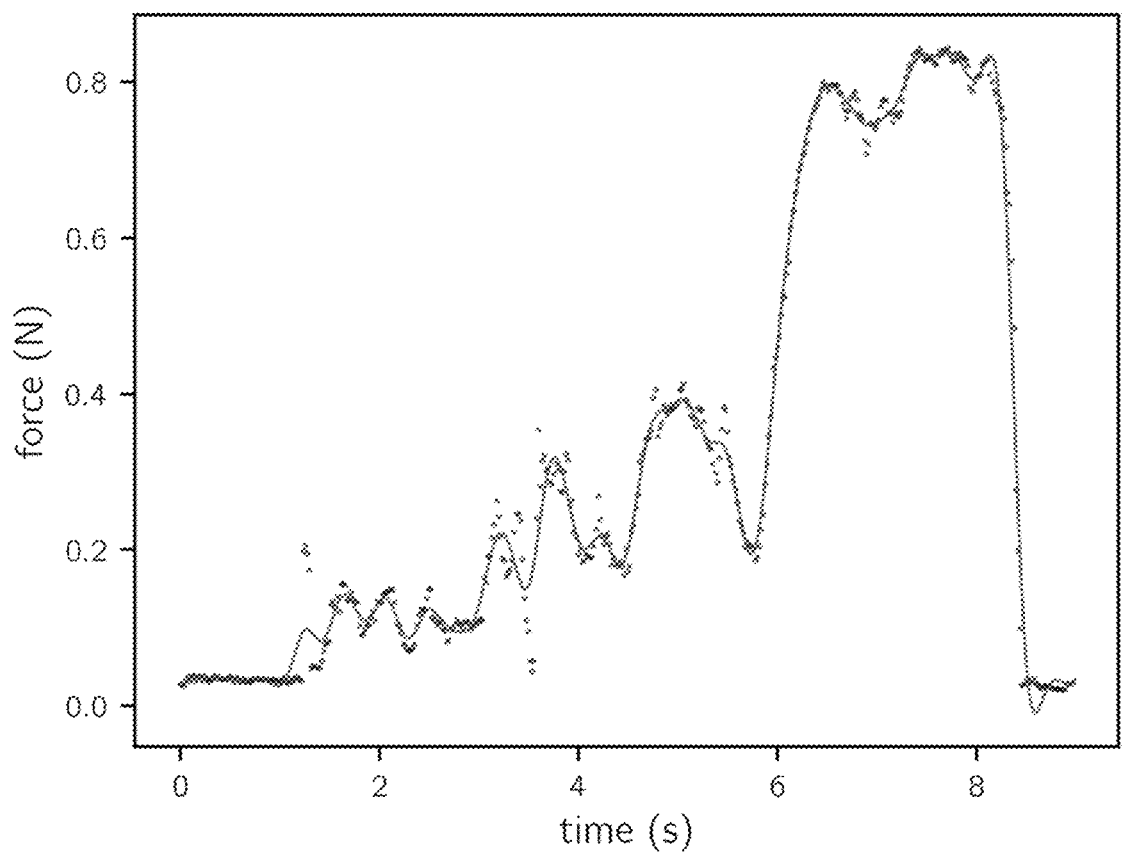
FIG. 10d is an example force profile showing a predicted unsuccessful injection.

FIG. 10d is an example force profile showing a predicted unsuccessful injection.

Figure 11:
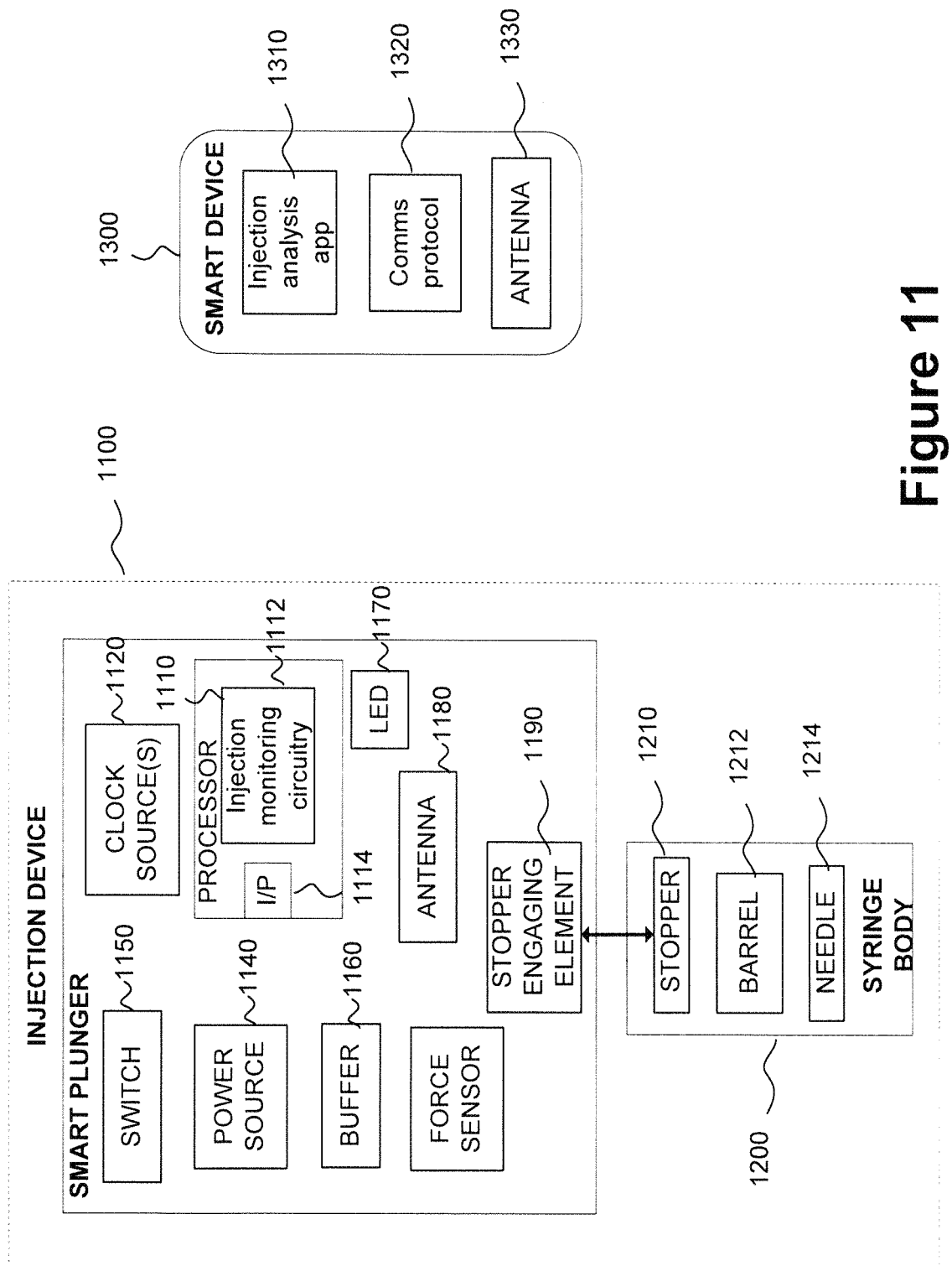
FIG. 11 schematically illustrates an example system architecture for a smart plunger for an injection device.

FIG. 11 schematically illustrates a system architecture for a smart plunger for an injection device 1100. The injection device 1100 includes a smart plunger 1120 having a processor 1110, including injection monitoring circuitry 1112 and an input interface 1114 and further including a clock source 1120, a force sensor 1130, a power source 1140, switch 1150, a buffer 1160, a light emitting device 1170 to indicate if the device is on or off, an antenna 1180 to communicate with a smart device 1300 and a stopper engaging element 1190 to engage with a resilient stopper 1210 of a syringe body 1200. The syringe body 1200 has the resilient stopper 1210, a syringe barrel 1212 and a needle 1214. Optionally, the syringe body 1200 includes a needle safety device (not shown).

The injection device 1100 is arranged to wirelessly communicate with the smart device 1300. The smart device 1300 has an injection analysis application 1310 installed thereon and may implement a wireless communication protocol 1320 such as a Bluetooth Low Energy communication protocol. The smart device also has an antenna 1330 to communicate wirelessly with a corresponding antenna 1180 of the smart plunger 1110. A user may download the injecting analysis app 1310 using, for example, a QR code. After pre-configuration of the injection analysis app 1310 for a user, the app may run in the background on the smart device such that the user need not actively pair the injection device 1100 with the smart device 1300. This increases the likelihood that the force profile and medicament injection compliance data is captured because of the automatic pairing. The smart device 1300 may not belong to the particular user of the injection device, but instead may act as a conduit to transfer force profile data to the cloud platform 160 (see FIG. 1).

The smart plunger 1120 may communicate unencrypted data in a Bluetooth advertising message using a Bluetooth low energy protocol to send data to the smart device 1300 and in particular, to the communications protocol circuitry 1320. Encrypted data may be stored in the injection analysis app 1310 relating to, for example, an injection time, force profile data and an injection device identification code. A Wi-Fi or long-term evolution (LTE) mobile telecommunication service may be used to communicate encrypted injection and patient data to authorised users of the cloud platform 160 (see FIG. 1). The force profile data may be broadcast opportunistically from the antenna 1180 of the smart plunger 1120 to any enabled smart device such as the smart device 1300 in range of the smart plunger 1120. Additional confidential patient data may be appended to the force profile data in the smart device 1300 before encryption.

The stopper engaging element 1190 of the smart plunger may engage with the stopper 1210 of the syringe body the via a screw-fit, a snap-coupling or a magnetic coupling for example and upon engagement of the stopper and the stopper engaging element, the switch 1150 powers up the processor 1110 and the corresponding injection monitoring circuitry 1112 such that when the injection device 1100 is ready to perform an injection event and up the injection monitoring circuitry 1112 is active and ready to capture the force profile detected by the force sensor 1130. The LED 1170 may indicate when the injection monitoring circuitry 1112 has switched on as a result of engagement between the stopper 1210 and the stopper engaging element 1190. The power source 1140 may be, for example, a replaceable battery operable to power monitoring of up to at least fifty injection events before it is replaced.

Force profile data is captured by the injection monitoring circuitry by time stamping force measurements obtained by the force sensor 1130 using the clock source 1120. The clock source 1120 may be for example a 16 MHz crystal or a 32 kHz crystal. The buffer 1160 is operable to store timestamp force measurements corresponding to the force profile and the injection monitoring circuitry 1112 is arranged to perform statistical analysis of the stored force profile data based on a deployed machine learning model.

The smart device 1300 may display to the user a current status of the injection device to display, for example, information to assist a user with injection technique. The smart device 1300 may display on a display screen a scaled force profile to allow a user to monitor progress of an injection event. The calculation of the scaling prior to user display may be performed on the smart device 1300. The smart device 1300 may indicate an end of injection event detected by the machine learning algorithm implemented by the processor 1110.

According to the present technique, the plunger rod having injection monitoring circuitry 1112 is operable to identify when the plunger rod has bottomed out in a barrel of the syringe and to provide an injection complete notification indicative that a complete dose of a medicament has been delivered during an injection event. Injection force profiles may be recorded via the buffer 1160 of the smart plunger 1120 and these injection profiles provide information revealing how users interact with the injection device facilitating future design improvements. Furthermore, characteristics of the force profiles enable manufacturing issues to be identified from batch to batch where injection device identification information is appended to the force profile data. The force profile data may be analysed in order to assess whether or not drug effectiveness is linked to injection rate or time of injection, for example. Furthermore, the force profiles enable per injection technique for individual users to be identified and for guidance to be provided to users via the smart device 1300 to improve injection technique in real-time. Furthermore, characteristics of individual force profiles for a given user on different dates allow a changing grip strength to be detected and tracked, which may be useful to track developing conditions such as multiple sclerosis or rheumatoid arthritis.

From the processed force profile data collected by the injection monitoring circuitry, at least any of the following example characteristics can be determined:
   a) the time and date an injection has been delivered;
   b) the size of needle being used (calculated from the flow rate and injection duration);
   c) the grip strength of the user;
   d) the duration of an injection ("injection time");
   e) the duration of the needle remaining in the injection site after delivery of medicament ("hold time"); and
   f) when the plunger rod reaches its furthest distal position in order to provide an "injection complete" feedback notification to the user;

Recording and processing data over a period of time including a number of injections can provide useful data particular to the specific user. For example, poor injection technique can be identified from the force profiles recorded. The combination of injection time plus hold time is a particularly useful characteristic to determine. An injection delivered relatively slowly needs less hold time. If the user tends to deliver the injection too quickly, feedback can be given to encourage a slower, more gentle, injection requiring less hold time, thus promoting good injection technique.

The injection monitoring circuitry 1112 could recognize the contents of a particular prefilled syringe (for example using RFID), allowing it to capture and correlate data on multiple drugs Over a period of time, collection of data from many discrete users can also have useful benefits. For example, recording the force profile of many injections enables a picture to be built up of how users interact with the device. Collection of data from many users could assist in improving future syringe design. Manufacturing issues, for example insufficient or excessive siliconization of the syringe barrel could be determined.

Collection of data from many users over a period time may also have clinical benefits. For example, the data could be used to assess whether the effectiveness of a particular drug is linked to injection rate, injection time+hold time, or other characteristics.

The reusable nature of the plunger rod 120 incorporating the injection monitoring circuitry 1112 reduces cost and eases concerns about the waste and disposability of electronic and non-recyclable components.

The reusable nature of the plunger rod 120 enhances the user experience by providing a personalised object, customisable for the individual user.

A standard prefilled syringe would be supplied to the user without a plunger rod fitted so that it is essential to use the personal reusable plunger rod 120. By supplying the prefilled syringes without a plunger rod, packaging can be reduced, also reducing the cost of storage and distribution.

An "emergency plunger" (which does not include injection monitoring circuitry) could potentially be supplied for occasions when the user's reusable plunger rod 120 is not to hand.

By supplying the prefilled syringes without a plunger rod, safety is improved in that small children for example cannot pick up and deliver medicament from the syringe unsupervised.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. Embodiments of the invention extend to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

In this specification, the phrase "at least one of A or B" and the phrase "at least one of A and B" and should be interpreted to mean any one or more of the plurality of listed items A, B etc., taken jointly and severally in any and all permutations.

Where functional units have been described as circuitry, the circuitry may be general purpose processor circuitry configured by program code to perform specified processing functions. The circuitry may also be configured by modification to the processing hardware. Configuration of the circuitry to perform a specified function may be entirely in hardware, entirely in software or using a combination of hardware modification and software execution. Program instructions may be used to configure logic gates of general purpose or special-purpose processor circuitry to perform a processing function.

Circuitry may be implemented, for example, as a hardware circuit including processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate arrays (FPGAs), logic gates, registers, semiconductor devices, chips, microchips, chip sets, and the like.

The processors may include a general purpose processor, a network processor that processes data communicated over a computer network, or other types of processor including a reduced instruction set computer RISC or a complex instruction set computer CISC. The processor may have a single or multiple core design. Multiple core processors may integrate different processor core types on the same integrated circuit die Machine readable program instructions may be provided on a transitory medium such as a transmission medium or on a non-transitory medium such as a storage medium. Such machine-readable instructions (computer program code) may be implemented in a high level procedural or object-oriented programming language. However, the program(s) may be implemented in assembly or machine language, if desired. In any case, the language may be a compiled or interpreted language, and combined with hardware implementations.

Embodiments of the present invention are applicable for use with all types of semiconductor integrated circuit ("IC") chips. Examples of these IC chips include but are not limited to processors, controllers, chipset components, programmable logic arrays (PLAs), memory chips, network chips, and the like. In some embodiments, one or more of the components described herein may be embodied as a System On Chip (SOC) device. A SOC may include, for example, one or more Central Processing Unit (CPU) cores, one or more Graphics Processing Unit (GPU) cores, an Input/Output interface and a memory controller. In some embodiments a SOC and its components may be provided on one or more integrated circuit die, for example, packaged into a single semiconductor device.

What is claimed is:

1. Injection monitoring circuitry for coupling to part of an injection device having a syringe and a plunger rod, the injection monitoring circuitry comprising:
   an input to receive force measurement data from a force sensor, the force measurement data comprising a plurality of timestamped force measurements of force applied by a user to the injection device when an injection is administered to an injection site; and
   processing circuitry configured to determine from the force measurement data when an end of injection has been reached, the end of injection corresponding to the plunger rod having reached an end position in a distal portion of a barrel of the syringe during administration of the injection by the user,
   wherein the processing circuitry is configured to determine the end of injection from a force profile for an injection administering event, the force profile comprising an ordered time series of the plurality of timestamped force measurements, and wherein the processing circuitry is configured to determine a displacement of the plunger rod within the syringe as a function of time by integrating an area under a characteristic curve fitted to the force profile.

2. Injection monitoring circuitry of claim 1, wherein the processing circuitry is configured to determine from the force profile at least one of: a start of injection corresponding to a start of a transfer of a medicament from the syringe barrel to the injection site, a duration of the injection and whether or not a full dose of a medicament has been delivered by the end of the injection.

3. Injection monitoring circuitry of claim 1, wherein the processing circuitry is configured to scale the force measurement data using at least one scaling factor, the scaling factor being selected depending on a form factor of a wirelessly connected display device remote from the injection device on which a force profile incorporating the force measurement data is to be displayed.

4. Injection monitoring circuitry of claim 1, wherein the processing circuitry is configured to determine an injection hold time corresponding to a duration that a needle of the syringe is to remain in an injection site after the end of the injection and to output an indication of the injection hold time to the user.

5. An injection device comprising the injection monitoring circuitry of claim 1 and a plunger rod, the plunger rod comprising the injection monitoring circuitry.

6. The injection device of claim 5, wherein at least a portion of the injection monitoring circuitry is provided in a proximal head of the plunger rod.

7. Injection monitoring circuitry for coupling to part of an injection device having a syringe and a plunger rod, the injection monitoring circuitry comprising:

an input to receive force measurement data from a force sensor, the force measurement data comprising a plurality of timestamped force measurements of force applied by a user to the injection device when an injection is administered to an injection site; and processing circuitry configured to determine from the force measurement data when an end of injection has been reached, the end of injection corresponding to the plunger rod having reached an end position in a distal portion of a barrel of the syringe during administration of the injection by the user, wherein the processing circuitry is configured to determine the end of injection from a force profile for an injection administering event, the force profile comprising an ordered time series of the plurality of timestamped force measurements, and wherein the processing circuitry is configured to determine a displacement of the plunger rod within the syringe as a function of time by integrating an area under a characteristic curve fitted to the force profile, and wherein the end of injection is determined using at least one of: wavelet convolution of the force profile and Fourier analysis of the force profile.

8. Injection monitoring circuitry of claim 7, wherein the processing circuitry is configured to implement a state machine on the force profile to determine at least one of a possible injection start time and a possible injection end time.

9. Injection monitoring circuitry of claim 8, wherein the processing circuitry is configured to determine the end of injection by implementing a neural network algorithm.

10. Injection monitoring circuitry of claim 8, wherein the processing circuitry is configured to determine the end of injection by implementing a machine learning algorithm on an analysis time window of the force profile selected based on the possible injection start time and the possible injection end time determined by the state machine.

11. Injection monitoring circuitry of claim 10, wherein the processing circuitry is configured to implement the machine learning algorithm to analyse a plurality of predetermined features of the force profile in the analysis time window to determine the end of injection, the predetermined features comprising at least a subset of: an injection duration; a mean force magnitude; a standard deviation of force measurements; a skew of force measurements; a kurtosis of force measurements; a maximum force value; a minimum force value; a $25^{th}$ percentile value; and a $75^{th}$ percentile value.

12. Injection monitoring circuitry of claim 10, wherein the processing circuitry is configured to implement the machine learning algorithm to analyse a plurality of predetermined features of the force profile in the analysis time window by sub-dividing the analysis time window into a plurality of time intervals and performing the features analysis for at least one of the predetermined features independently for each of at least two of the plurality of time intervals.

13. Injection monitoring circuitry of claim 12, wherein the at least one predetermined feature independently analysed for the at least two time intervals is a mean force in the time interval or a standard deviation of the force in the time interval.

* * * * *